US009726642B2

(12) United States Patent
Park et al.

(10) Patent No.: US 9,726,642 B2
(45) Date of Patent: Aug. 8, 2017

(54) ULTRASOUND BASED MEASUREMENT APPARATUS AND METHOD

(71) Applicant: SAMSUNG ELECTRONICS CO., LTD., Suwon-si (KR)

(72) Inventors: Sung Chan Park, Suwon-si (KR); Joo Young Kang, Yongin-si (KR); Kyu Hong Kim, Seoul (KR); Jung Ho Kim, Yongin-si (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 289 days.

(21) Appl. No.: 14/612,902

(22) Filed: Feb. 3, 2015

(65) Prior Publication Data

US 2015/0226850 A1   Aug. 13, 2015

(30) Foreign Application Priority Data

Feb. 13, 2014   (KR) .................. 10-2014-0016381

(51) Int. Cl.
*G01S 7/52*    (2006.01)
*G01S 15/89*   (2006.01)
*G01N 29/06*   (2006.01)

(52) U.S. Cl.
CPC ....... *G01N 29/0663* (2013.01); *G01N 29/069* (2013.01); *G01S 7/52049* (2013.01); *G01S 15/8997* (2013.01); *G01N 2291/106* (2013.01)

(58) Field of Classification Search
CPC ............. G01N 29/069; G01N 29/0663; G01N 2291/106; G01S 7/52049; G01S 15/8997

USPC .......................................................... 73/603
See application file for complete search history.

(56) References Cited

U.S. PATENT DOCUMENTS

| | | | | |
|---|---|---|---|---|
| 5,503,152 A | * | 4/1996 | Oakley | ............... A61B 8/08 128/916 |
| 5,517,995 A | * | 5/1996 | Klepper | ............... B06B 1/0629 600/437 |
| 5,570,691 A | | 11/1996 | Wright et al. | |
| 5,581,517 A | | 12/1996 | Gee et al. | |
| 5,673,699 A | | 10/1997 | Trahey et al. | |
| 5,760,904 A | * | 6/1998 | Lorraine | ............... G01B 11/16 356/513 |

(Continued)

FOREIGN PATENT DOCUMENTS

| | | |
|---|---|---|
| JP | 2003-521341 A | 7/2003 |
| JP | 2008-507322 A | 3/2008 |

(Continued)

OTHER PUBLICATIONS

G. Hayward, et al., "Low power ultrasonic imaging using digital correlation", Ulttrasonics, IPC Science and Technology Press Ltd., Guildford, GB, vol. 27, No. 5, Sep. 1, 1989 p. 288-296, XP025720218.

(Continued)

*Primary Examiner* — J M Saint Surin
(74) *Attorney, Agent, or Firm* — Sughrue Mion, PLLC

(57) ABSTRACT

An ultrasound based measurement method includes obtaining an element of synthetic data corresponding to a focusing point in a region adjacent to a reflector by applying a synthetic focusing method to received data corresponding to an actual focusing point; and generating an image of the reflector based on the element of the synthetic data.

24 Claims, 38 Drawing Sheets

(56) References Cited

U.S. PATENT DOCUMENTS

| | | | |
|---|---|---|---|
| 5,902,244 A | 5/1999 | Kobayashi et al. | |
| 6,208,283 B1* | 3/2001 | Murata | G01S 5/14 |
| | | | 342/190 |
| 6,292,433 B1* | 9/2001 | Gilbert | G01S 7/52085 |
| | | | 367/138 |
| 6,436,047 B1* | 8/2002 | Ramamurthy | G01S 7/52047 |
| | | | 600/447 |
| 6,602,194 B2 | 8/2003 | Roundhill et al. | |
| 6,607,489 B2 | 8/2003 | Hoctor et al. | |
| 6,699,189 B1 | 3/2004 | Lin et al. | |
| 7,540,842 B2 | 6/2009 | Napolitano et al. | |
| 2012/0004550 A1 | 1/2012 | Katsuyama | |
| 2012/0035480 A1* | 2/2012 | Migita | A61B 8/5269 |
| | | | 600/443 |
| 2013/0308850 A1* | 11/2013 | Oikawa | G01S 7/52085 |
| | | | 382/131 |
| 2014/0046187 A1* | 2/2014 | Taniguchi | A61B 8/5269 |
| | | | 600/444 |
| 2014/0071792 A1* | 3/2014 | Yoo | G01S 7/52047 |
| | | | 367/103 |

FOREIGN PATENT DOCUMENTS

| | | |
|---|---|---|
| JP | 2012-10875 A | 1/2012 |
| KR | 10-2012-0030488 A | 3/2012 |

OTHER PUBLICATIONS

Communication from the European Patent Office issued Aug. 24, 2015 in a counterpart European Application No. 14189722.3.

* cited by examiner

FIG. 4C

|  | 441 | 442 | 443 | 444 | 445 |
|---|---|---|---|---|---|
| n=1 | Ch1 data | Ch2 data | Ch3 data | Ch4 data | Ch5 data |
| n=2 | Ch1 data | Ch2 data | Ch3 data | Ch4 data | Ch5 data |
|  | 451 | 452 | 453 | 454 | 455 |

| n=25 | Ch1 data | Ch2 data | Ch3 data | Ch4 data | Ch5 data |
|---|---|---|---|---|---|

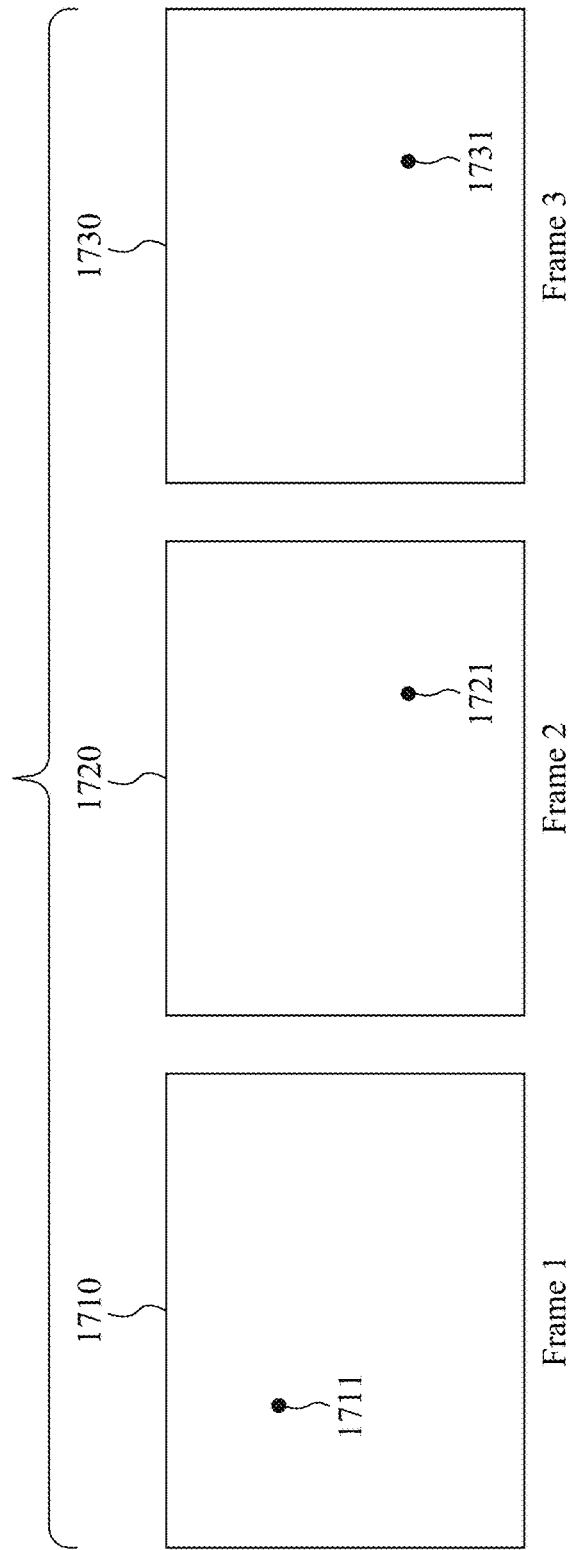

ULTRASOUND BASED MEASUREMENT APPARATUS AND METHOD

CROSS-REFERENCE TO RELATED APPLICATION

This application claims priority from Korean Patent Application No. 10-2014-0016381, filed on Feb. 13, 2014, in the Korean Intellectual Property Office, the disclosure of which is incorporated herein by reference in its entirety.

BACKGROUND

1. Field

Methods and apparatuses consistent with exemplary embodiments relate to an ultrasound based measurement apparatus and method, and more particularly, to an ultrasound based measurement apparatus and method that may measure an image of a reflector in a sample.

2. Description of the Related Art

An ultrasound based measurement apparatus may transmit an ultrasonic signal to a focusing point in a sample, receive an acoustic field reflected from a reflective point, e.g., a reflector in the sample, and measure an image of the reflector in the sample using the received acoustic field. For example, the ultrasound based measurement apparatus may process an image of the sample in real time and, thus, various applications may be found in various fields, for example, a biopsy and a nondestructive inspection.

The ultrasound based measurement apparatus may include a plurality of transducers and perform beamfocusing on a predetermined point in the sample by adjusting a transmission time of each transducer. The ultrasound based measurement apparatus may transmit an ultrasonic signal by performing the beamfocusing and measure the image of the reflector using the acoustic field reflected or scattered by the reflector.

However, when another reflector is also present in the sample in addition to the reflector desired to be measured, an acoustic field from another reflector may interfere with the acoustic field of the desired reflector. Accordingly, an accurate measurement of the image of the desired reflector may be difficult to perform.

SUMMARY

Exemplary embodiments may address at least the above problems and/or disadvantages and other disadvantages not described above. However, the exemplary embodiments are not required to overcome the disadvantages described above, and an exemplary embodiment may not overcome any of the problems described above.

According to an aspect of an exemplary embodiment, there may be provided an ultrasound based measurement method including obtaining at least one element of synthetic data corresponding to at least one focusing point in a region adjacent to a reflector by applying a synthetic focusing method to received data corresponding to at least one actual focusing point, and generating an image of the reflector based on the element of synthetic data.

The ultrasound based measurement method may further include performing ultrasonic beamfocusing on the actual focusing point, and obtaining the received data by receiving an acoustic field generated by the reflector in response to an ultrasonic signal.

The obtaining of the element of synthetic data may be performed by generating a plurality of synthetic data using the synthetic focusing method, and the generating of the image of the reflector may be performed using the plurality of synthetic data.

The obtaining of the element of synthetic data may include determining the element of synthetic focusing point in the region adjacent to the reflector, and estimating a first delay between the element of synthetic focusing point and the actual focusing point.

The obtaining of the element of synthetic data may include estimating a delay associated with each of at least one transducer based on the first delay, and performing delay correction on the received data, based on the estimated delay, for each channel of the transducer.

The obtaining of the element of synthetic data may include performing the delay correction on each synthetic focusing point, and obtaining synthetic data corresponding to each synthetic focusing point.

The obtaining of the image of the reflector may include generating single channel data by calculating a sum of the synthetic data of each synthetic focusing point for each channel, and obtaining the image of the reflector based on the single channel data.

The obtaining of the image of the reflector may further include performing aberration correction on the single channel data.

The ultrasound based measurement method may further include performing motion correction on the received data.

The performing of the motion correction may further include obtaining image frames of the reflector based on the received data, and detecting a motion vector of the reflector by a comparison of the image frames.

The ultrasound based measurement method may further include estimating a second delay between a location of the reflector prior to a motion and a location of the reflector subsequent to the motion, estimating a delay associated with each of at least one transducer based on the estimated second delay, and performing delay correction on the received data based on the estimated delay, for each channel of the transducer.

The performing of the delay correction may include performing the delay correction on received data in a sampling section corresponding to an image frame from which the motion vector is detected, for each channel of the transducer, based on a location of the reflector in an initial image frame.

The generating of the image of the reflector may be performed using the element of synthetic data and the received data.

According to an aspect of an exemplary embodiment, there may be provided an ultrasound based measurement apparatus including a synthetic data obtainer which obtains at least one element of synthetic data corresponding to at least one element of synthetic focusing point in a region adjacent to a reflector by applying a synthetic focusing method to received data corresponding to at least one actual focusing point, and an image generator which generates an image of the reflector using the element of synthetic data.

The ultrasound based measurement apparatus may further include a data addition and aberration corrector which generates single channel data by calculating a sum of synthetic data of each synthetic focusing point for each channel and performs aberration correction on the single channel data.

The image generator may generate image frames based on the received data prior to generation of the synthetic data, and the ultrasound based measurement apparatus may further include a motion corrector which corrects a motion of the reflector based on the image frames.

The ultrasound based measurement apparatus may further include a motion estimator which performs a comparison of the image frames and detects a motion vector of the reflector.

According to an aspect of an exemplary embodiment, there may be provided an ultrasound based measurement apparatus including at least one transducer which performs ultrasonic beamfocusing on at least one actual focusing point and receives an acoustic field generated by a reflector in response to the ultrasonic beamfocusing, and a processor which obtains received data for each channel of the transducer, obtains synthetic data of each synthetic focusing point in a region adjacent to the reflector by applying a synthetic focusing method to the received data, and obtains an image of the reflector based on the synthetic data, for each channel of the transducer.

According to an aspect of an exemplary embodiment, there may be provided an ultrasound based measurement apparatus including an ultrasonic signal transceiver which transmits an ultrasonic signal to at least one actual focusing point and receives an acoustic field generated by a reflector in response to beamfocusing, an image generator which generates image frames based on received data received by the ultrasonic signal transceiver, a motion estimator which estimates a motion of the reflector based on the generated image frames, and a motion corrector which performs motion correction on the received data based on the estimated motion.

The ultrasound based measurement apparatus may further include a synthetic data obtainer which generates the synthetic data corresponding to multiple points in a region adjacent to the reflector by applying a synthetic focusing method to received data obtained subsequent to the motion correction, and a data addition and aberration corrector which generates single channel data by calculating a sum of the synthetic data for each channel and performs aberration correction. The image generator may generate the image of the reflector using the single channel data obtained subsequent to the aberration correction.

According to an aspect of an exemplary embodiment, there may be provided an ultrasound based measurement method including outputting a transducer controlling signal which controls a transducer to perform ultrasonic beamfocusing on at least one actual focusing point, receiving received data with respect to an acoustic field generated by a reflector in response to the ultrasonic beamfocusing, obtaining synthetic data of each multiple synthetic focusing point in a region adjacent to the reflector based on a synthetic focusing method, and obtaining an image of the reflector based on the synthetic data.

According to an aspect of an exemplary embodiment, there may be provided an ultrasound based measurement method including outputting a transducer controlling signal which controls a transducer to perform actual ultrasonic beamfocusing, receiving received data with respect to an acoustic field generated by a reflector in response to the actual ultrasonic beamfocusing, extracting a harmonic component from the received data, obtaining synthetic data of each multiple synthetic focusing point in a region adjacent to the reflector based on a synthetic focusing method, and obtaining an image of the reflector based on the synthetic data.

The ultrasound based measurement method may include outputting the transducer controlling signal which controls the transducer to perform beamfocusing by allowing an ultrasonic signal to be positioned behind the transducer from at least one actual focusing point, receiving the received data with respect to the acoustic field generated by the reflector in response to the actual ultrasonic beamfocusing, obtaining the synthetic data for each of the multiple synthetic focusing points in the region adjacent to the reflector based on the synthetic focusing method, and obtaining the image of the reflector based on the synthetic data.

BRIEF DESCRIPTION OF THE DRAWINGS

The above and/or other aspects will become more apparent by describing certain exemplary embodiments with reference to the accompanying drawings, in which:

FIGS. 4C and 4D are diagrams which illustrate received data and addition of the received data for each channel according to an exemplary embodiment;

FIG. 17B is a diagram which illustrates multiple image frames according to an exemplary embodiment;

DETAILED DESCRIPTION

Figure 1A:
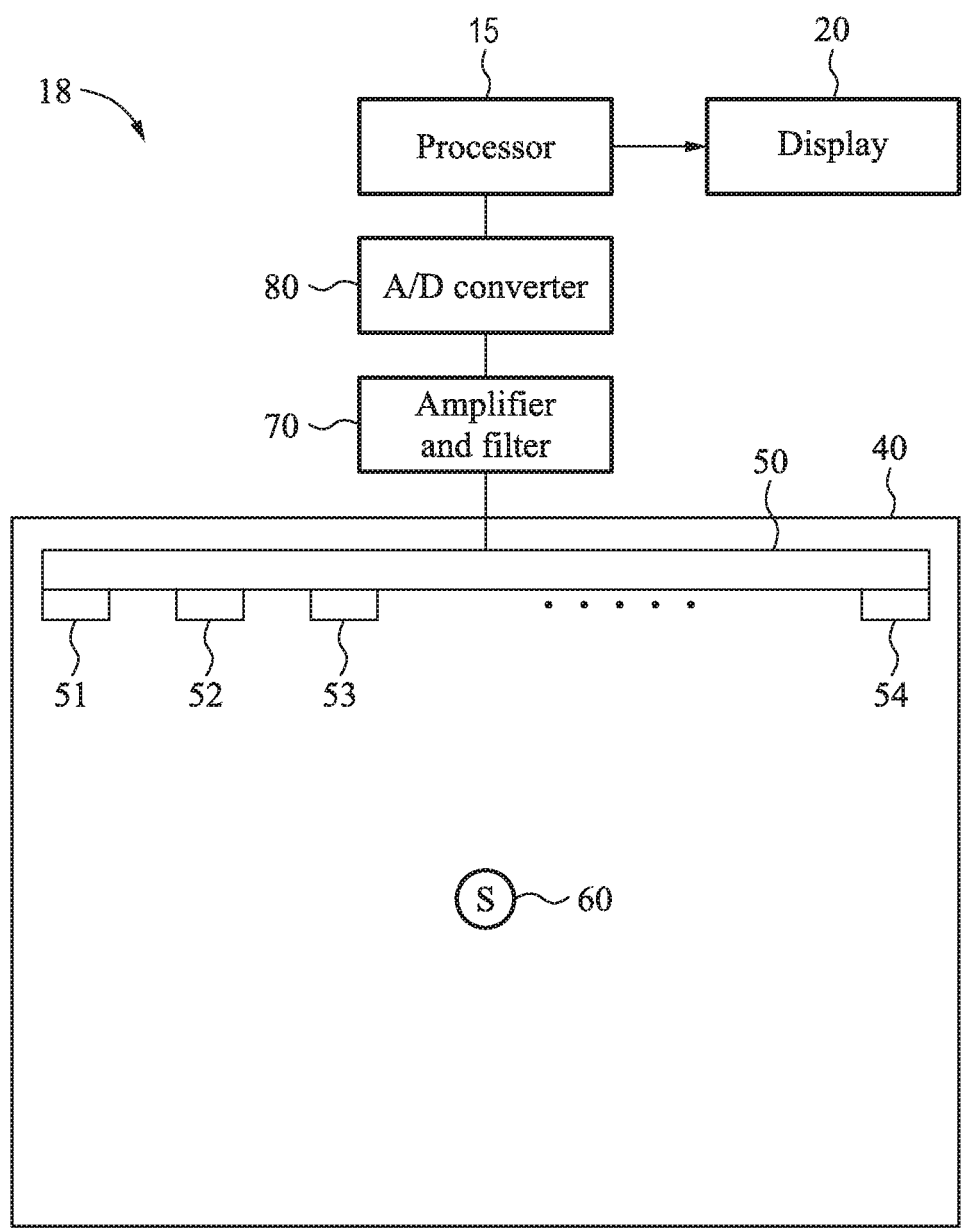
FIGS. 1A and 1B are diagrams which illustrate an ultrasound based measurement apparatus according to exemplary embodiments.

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

Figure 1B:
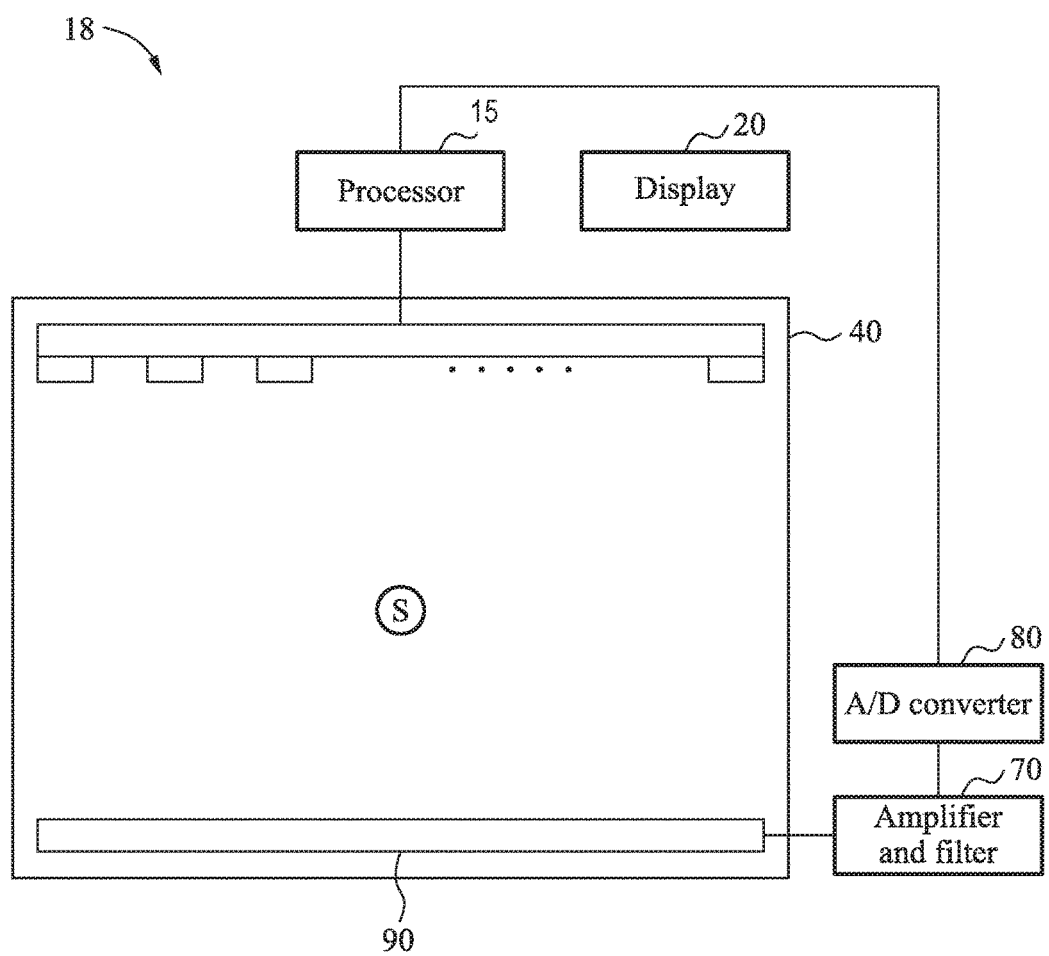

FIGS. 1A and 1B are diagrams which illustrate examples of an ultrasound based measurement apparatus according to an exemplary embodiment.

Referring to FIG. 1A, the ultrasound based measurement apparatus 18 may include a processor 15, a display 20, a medium container 40, a transceiver 50, an amplifier and filter 70, and an analog to digital (A/D) converter 80. The transceiver 50 may include one or more transducers 51, 52, 53, . . . , 54.

The processor 15 may control operations of the ultrasound based measurement apparatus, for example, based on a program or an algorithm stored in a storage (not shown). The processor 15 may determine a transmission time and a transmission point of the transceiver 50. The transmission time may refer to a point in time at which an ultrasonic signal is transmitted from the transceiver 50, and the transmission point may refer to a point at which the ultrasonic signal is transmitted from the transceiver 50. The processor 15 may determine a beamfocusing point at which the ultrasonic signal is focused and an operation time of each transducer corresponding to the determined beamfocusing point. The processor 15 may generate an electrical signal with respect to the operation time of the transducer and output the generated electrical signal to each transducer. For example, the processor 15 may determine the transmission time for each transducer to allow an ultrasonic signal to be beamfocused on at least one focusing point in a sample 60.

Each transducer may convert an electrical signal to an ultrasonic signal and transmit an ultrasonic signal at the operation time based on the electrical signal received from the processor 15. Ultrasonic signals from the transducer may interfere with one another and may be beamfocused on a certain point.

The transducer may convert the received acoustic field to an electrical signal. The acoustic field may refer to a field in a medium reflected or scattered by a reflector in the sample 60. The converted electrical signal may be amplified and filtered based on a gain predetermined by the amplifier and filter 70. The filtered electrical signal may be converted to a digital signal by the A/D converter 80. The electrical signal to which the received acoustic field is converted or the digital signal may be referred to as received data. The received data may include data of each transducer channel, as described in detail below with reference to Table 1.

The transducer may receive the acoustic field during a certain period of time. The acoustic field to be received by each transducer may also be converted over time. Accordingly, the received data may be time-based data associated with the certain period of time. For example, the received data may be time series data based on a sampling period of time by the A/D converter 80.

The processor 15 may receive the received data and generate an image of the sample 60 based on the received data. The processor 15 may control the display 20 to display the generated image.

The processor 15 may determine the transmission time of the transducers to perform ultrasonic beamfocusing on at least one actual focusing point. For example, the processor 15 may obtain the received data for each transducer channel.

As described in greater detail below, the processor 15 may obtain synthetic data with respect to synthetic focusing points, i.e., non-existent focusing points, in a region adjacent to the reflector in the sample 60 using a synthetic focusing method, and obtain the image of the reflector based on the synthetic data.

The medium container 40 may be a medium used for movements of the ultrasonic signal. However, the medium container 40 may be omitted from the ultrasound based measurement apparatus in a measuring environment in which a medium is prepared in advance.

FIG. 1B is a diagram illustrating another example of an ultrasound based measurement apparatus 18. In contrast with the ultrasound based measurement apparatus of FIG. 1A, the ultrasound based measurement apparatus of FIG. 1B may further include a receiver 90 including a hydrophone having at least one channel or an additional transducer.

Figure 2A:
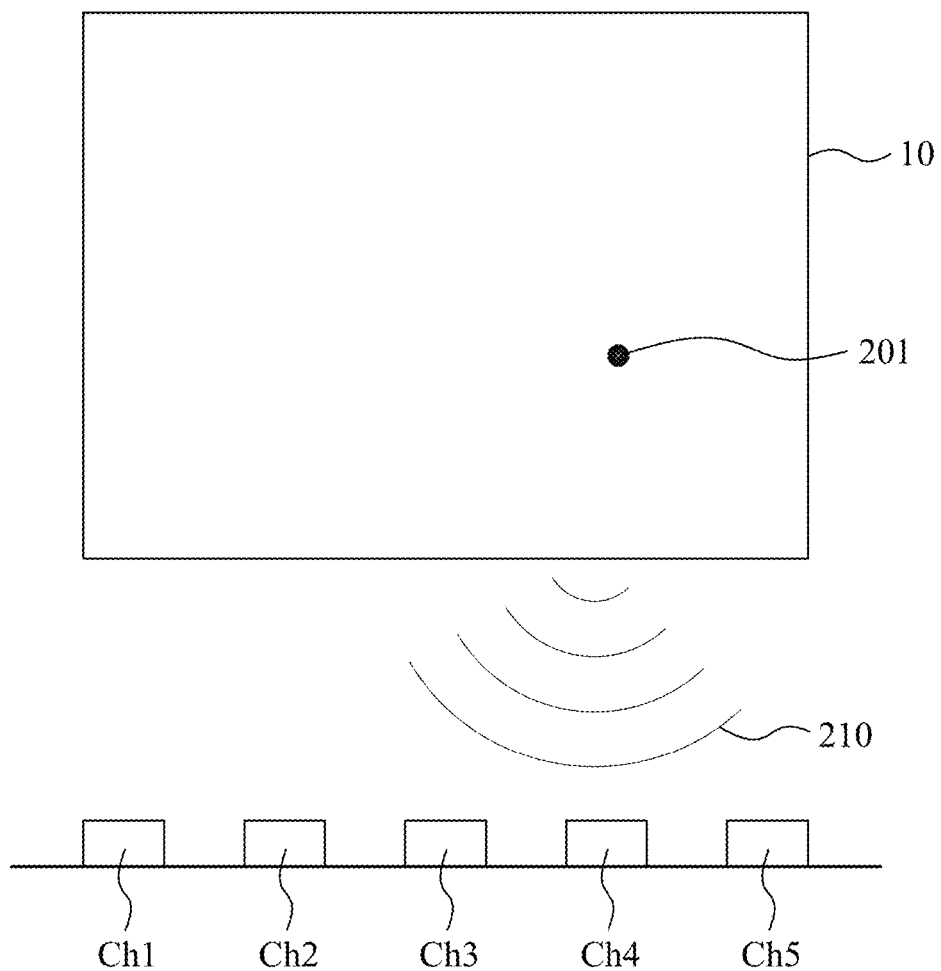
FIG. 2A is a diagram which illustrates an example in which a single reflector is present in a sample according to an exemplary embodiment.

FIG. 2A is a diagram which illustrates an example in which a single reflector 201 is present in a sample 10 according to an exemplary embodiment.

Although not illustrated in FIG. 2A, at least one transducer, for example, from transducers designated Ch. 1, Ch. 2, Ch. 3, Ch. 4 and Ch. 5, may transmit an ultrasonic signal to the sample 10. The sample 10 may receive the ultrasonic signal and generate an acoustic field 210 in response to the received ultrasonic signal. The single reflector 201 may be included in the sample 10. The single reflector 201 may reflect the acoustic field 210 in response to the ultrasonic signal from the transducer or an ultrasonic signal from a beamfocusing field.

The transducer may receive the acoustic field 210 and convert the received acoustic field 210 to an electrical signal. An ultrasound based measurement apparatus may detect a location of the reflector 201 based on the converted signal.

As illustrated in FIG. 2A, the acoustic field 210 generated by the single reflector 201 may be a substantially spherical wave. Based on Huygens' principle, a concentric acoustic field may be formed from the single reflector 201.

When the single reflector 201 reflects the acoustic field 210 as the substantially spherical wave, the ultrasound based measurement apparatus may perform spherical aberration correction and generate an image of the single reflector 201.

Figure 2B:
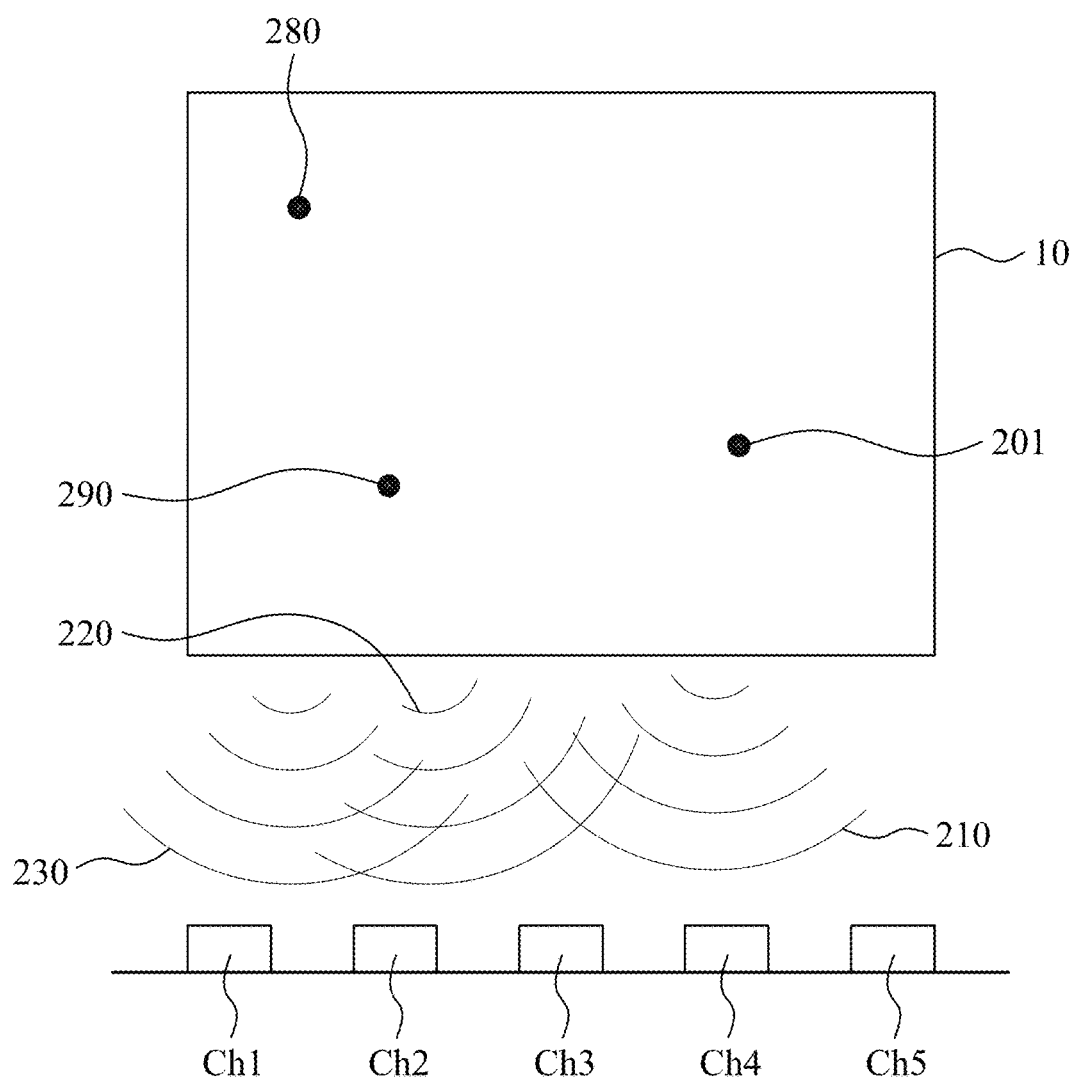
FIG. 2B is a diagram which illustrates an acoustic field when multiple reflectors are present in a sample according to an exemplary embodiment.

FIG. 2B is a diagram which illustrates acoustic fields, for example, 210, 220, and 230, generated when multiple reflectors, for example, 201, 280, and 290, are present in a sample 10 according to an exemplary embodiment.

At least one transducer, for example, from transducers Ch. 1 through Ch. 5, may transmit an ultrasonic signal to the sample 10. A reflector 201, 280, and/or 290 may receive the ultrasonic signal, and reflect an acoustic field 210, 220, and/or 230, respectively. The acoustic fields 210, 220, and 230 may interfere with one another in a medium.

As illustrated in FIG. 2B, the acoustic fields 210, 220, and 230 generated by the multiple reflectors 201, 280, and 290 respectively may be generated as substantially spherical waves which interfere with one another. When the acoustic field having the interference and having a waveform shape that is substantially different from the spherical form is input to the transducer, an ultrasound based measurement apparatus may generate an inaccurate image of a particular reflector, for example, the reflector 201.

Figure 3:
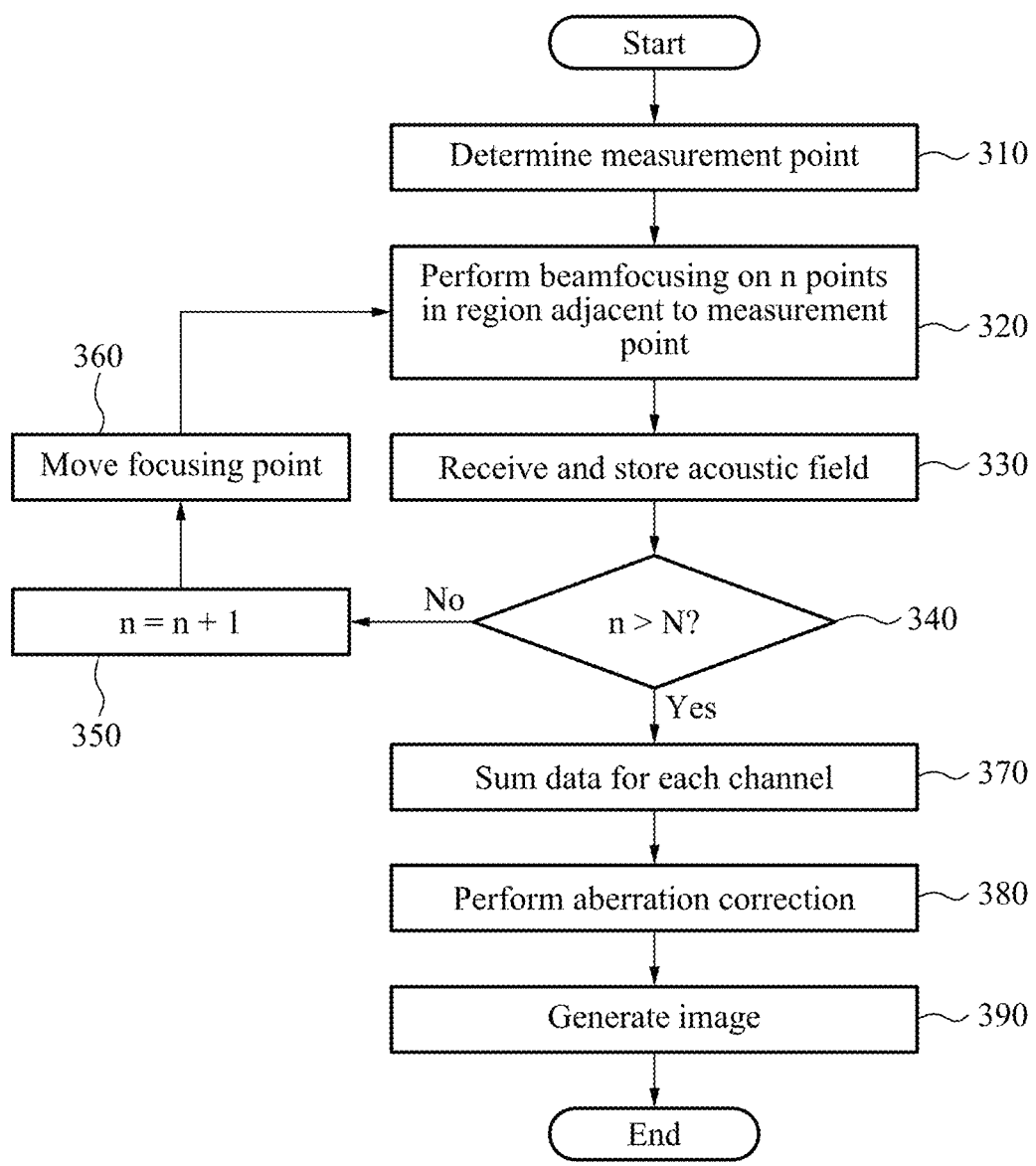
FIG. 3 is a flowchart which illustrates an example of an ultrasound based measurement method used for a sample in which another reflector is present in addition to a first reflector to be measured according to an exemplary embodiment.

FIG. 3 is a flowchart which illustrates an example of an ultrasound based measurement method used for a sample 10 in which another extraneous reflector is present in addition to a reflector to be measured according to an exemplary embodiment. The example illustrated in FIG. 3 will be further described with reference to FIGS. 4A through 4C.

Figure 4A:
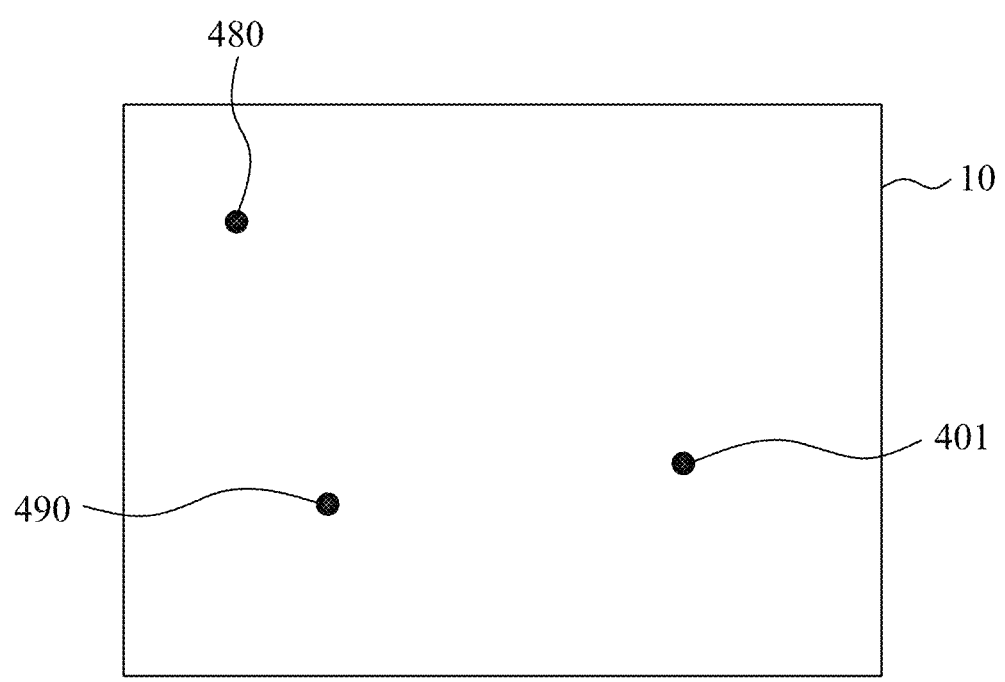
FIGS. 4A and 4B are diagrams which illustrate the ultrasound based measurement method of FIG. 3.

As illustrated in FIG. 4A, first, second, and third reflectors 401, 480, and 490 may be included in the sample 10.

Referring to FIG. 3, in operation 310, a measurement point may be determined. The measurement point may refer to a point required to generate an image. For example, the first reflector 401 may be determined as the measurement point. Based on a method to be described hereinafter, an influence that extraneous second and third reflectors 480 and 490 may have during measurement may be controlled and substantially minimized or eliminated.

Figure 4B:
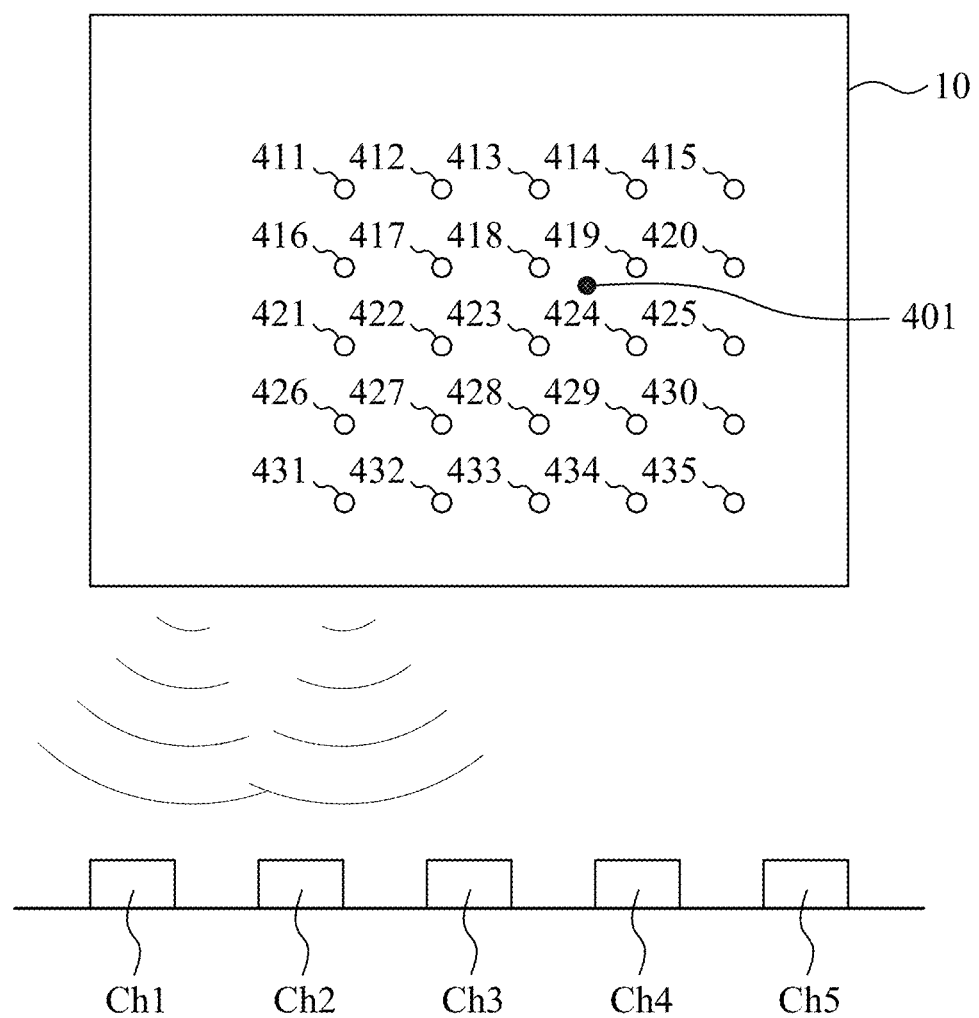

In operation 320, beamfocusing may be performed on n points in a region adjacent to the measurement point, as illustrated in FIG. 4B. An ultrasound based measurement apparatus according to an exemplary embodiment may include a plurality of transducers. The ultrasound based measurement method may adjust a transmission time of each transducer to transmit an ultrasonic signal. For example, the ultrasound based measurement method may output a transducer controlling signal including the transmission time of each transducer. Accordingly, the ultrasound based measurement method may perform the beamfocusing to focus an output ultrasonic signal on a particular point in the sample 10.

For example, when the beamfocusing is performed on a first point 411 of FIG. 4B, the ultrasound based measurement method may adjust the transmission time of a second transducer Ch. 2 to be relatively later and the transmission time of a fifth transducer Ch. 5 to be relatively earlier. For example, when a distance between the first point 411 and the second transducer Ch. 2 is smaller, and a distance between the first point 411 and the fifth transducer Ch. 5 is greater, an ultrasonic signal may be transmitted later in time from the second transducer Ch. 2 and an ultrasonic signal may be transmitted earlier in time from the fifth transducer Ch. 5.

Accordingly, multiple ultrasonic signals may be simultaneously focused at the first point 411. The ultrasound based measurement method may determine the transmission time of each transducer and thus, control ultrasonic signals transmitted from all of the transducers to simultaneously converge on the first point 411.

Figure 7A:
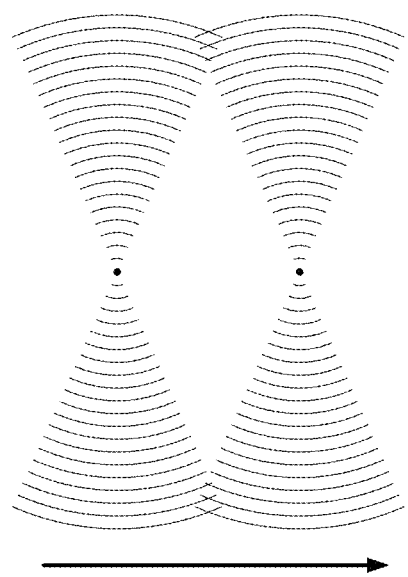
FIGS. 7A, 7B, and 7C are diagrams which illustrate examples in which beamfocusing is performed on a focusing point according to an exemplary embodiment.
Figure 7B:
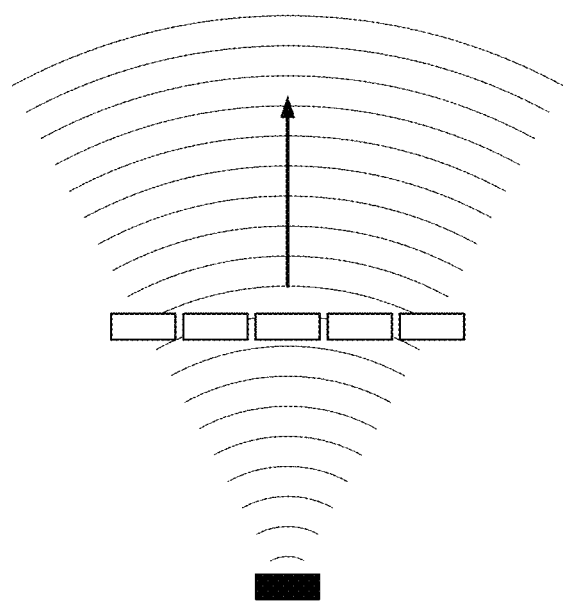

According to another exemplary embodiment, an ultrasound based measurement method may perform beamfocusing in a manner of an ultrasonic signal being generated from a second point, as shown in FIG. 7B. For example, the ultrasound based measurement method may determine the second point to be a point positioned behind a transducer, and perform the beamfocusing in a manner that ultrasonic waves are spread from the second point. For example, positions at which the ultrasonic waves are focused towards a depth direction for each scanline may differ from one another.

Subsequent to the beamfocusing performed on the first point 411, an acoustic field may be generated by a first reflector 401 of FIG. 4B. In operation 330, at least one transducer, for example, from transducers Ch. 1 through Ch. 5, may receive the acoustic field and convert the received acoustic field to an electrical signal. The ultrasound based measurement method may store received data of the received acoustic field for each channel, for example, Ch. 1 through Ch. 5. For example, the ultrasound based measurement method may store the received data for a predetermined duration. Examples of the stored received data corresponding to the first point 411 are provided in Table 1 below.

TABLE 1

| | Ch 1 | Ch 2 | Ch 3 | Ch 4 | Ch 5 |
|---|---|---|---|---|---|
| t = 1 | 21 | 30 | 20 | 10 | 8 |
| t = 2 | 29 | 40 | 28 | 14 | 11 |
| t = 3 | 37 | 50 | 36 | 21 | 16 |
| t = 4 | 46 | 60 | 45 | 28 | 20 |
| t = 5 | 51 | 50 | 50 | 33 | 23 |
| t = 6 | 38 | 40 | 37 | 37 | 26 |

In Table 1, the received data may be sampled and stored for a predetermined duration. In first column, values of t may denote a sampling number, i.e., 1 through 6. The received data may be stored by being classified based on the channel Ch. 1 through Ch. 5.

In operation 340, the ultrasound based measurement method may determine whether a value of n exceeds a value of N. For example, the value of N may be set to be equal to 25. When the value of n does not exceed the value of N, the ultrasound based measurement method may increase the value of n by 1 in operation 350, and move a focusing point in operation 360 in response to the increase. The ultrasound based measurement method may perform the beamfocusing on a second point 412 of FIG. 4B. The ultrasound based measurement method may readjust the transmission time for each of the transducers, Ch. 1 through Ch. 5, to correspond to the second point 412 and perform the beamfocusing on the second point 412.

The ultrasound based measurement method may determine focusing points, for example, focusing points 411, 412, 413, 414, 415, 416, 417, 418, 419, 420, 421, 422, 423, 424, 425, 426, 427, 428, 429, 430, 431, 432, 433, 434, and 435 of FIG. 4B, in a region adjacent to the first reflector 401, e.g., a measurement point. I.e., some focusing points may be disposed closer to the transducers than the first reflector 401, some focusing points may be disposed farther away from the transducers than the first reflector 401, and some focusing points may be disposed at the same distance as the first reflector 401 with respect to the transducers. For example, as illustrated in FIG. 4B, the focusing points 411 through 435 may be separated from one another at predetermined intervals and thus, the ultrasound based measurement method may determine a region in which the beamfocusing is to be performed to be in a form of a rectangular grid, with a first reflector 401 being disposed within the grid. Although FIG. 4B illustrates an example of the beamfocusing performed on 25 focusing points in a two-dimensional (2D) region, the example is provided only for an illustrative purpose and, thus, an ultrasound based measurement method according to another exemplary embodiment may perform the beamfocusing on, for example, 125 focusing points in a three-dimensional (3D) region.

The ultrasound based measurement method may perform the beamfocusing on all of the determined focusing points and store data of each focusing point for each channel.

For example, the ultrasound based measurement method may store received data as illustrated in FIG. 4C. The received data may be stored by each focusing point, for example, n=1, 2, . . . , 25. The received data of each focusing point may be stored for each channel. Received first data of the first focusing point 411 may be stored for each channel, for example, as a first channel first data 441, a second channel first data 442, a third channel first data 443, a fourth channel first data 444, and a fifth channel first data 445; received second data of the second focusing point 412 may be stored for each channel, for example, as a first channel second data 451, a second channel second data 452, a third channel second data 453, a fourth channel second data 454, and a fifth channel second data 455; etc. Each set of the data for each of the channels may be stored for a predetermined duration.

When all of the focusing points 411 through 435 of FIG. 4B are measured (n>N), the ultrasound based measurement method may calculate a sum of the received data for each channel in operation 370.

Figure 4D:
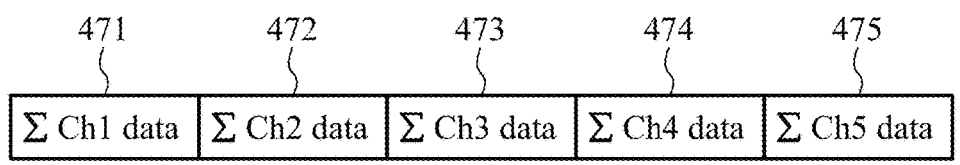

Referring to FIG. 4D, the ultrasound based measurement method may calculate a sum of 25 received data sets of the focusing points 411 through 435 for the first channel, for example, a sum of a first channel first data 441, a first channel second data 451, . . . etc., as a first channel data sum 471. Likewise, the ultrasound based measurement method may generate summed data other channels as, for example, a second channel data sum 472, a third channel data sum 473, a fourth channel data sum 474, and a fifth channel data sum 475, by calculating a sum of 25 received data sets of the focusing points 411 through 435 for each channel. Accordingly, the ultrasound based measurement method may generate single channel data, from 25 sets of the received data. That is, the single channel data may be a sum of multiple sets of the received data of multiple focusing points for each channel.

When data addition is performed for each channel, an influence of the acoustic fields by the extraneous second and third reflectors 480 and 490 may be offset.

In operation 380, the ultrasound based measurement method may perform aberration correction, described in greater detail below with reference to FIGS. 19 and 20. In operation 390, the ultrasound based measurement method may generate an image based on the calculated data for each channel.

Figure 4E:
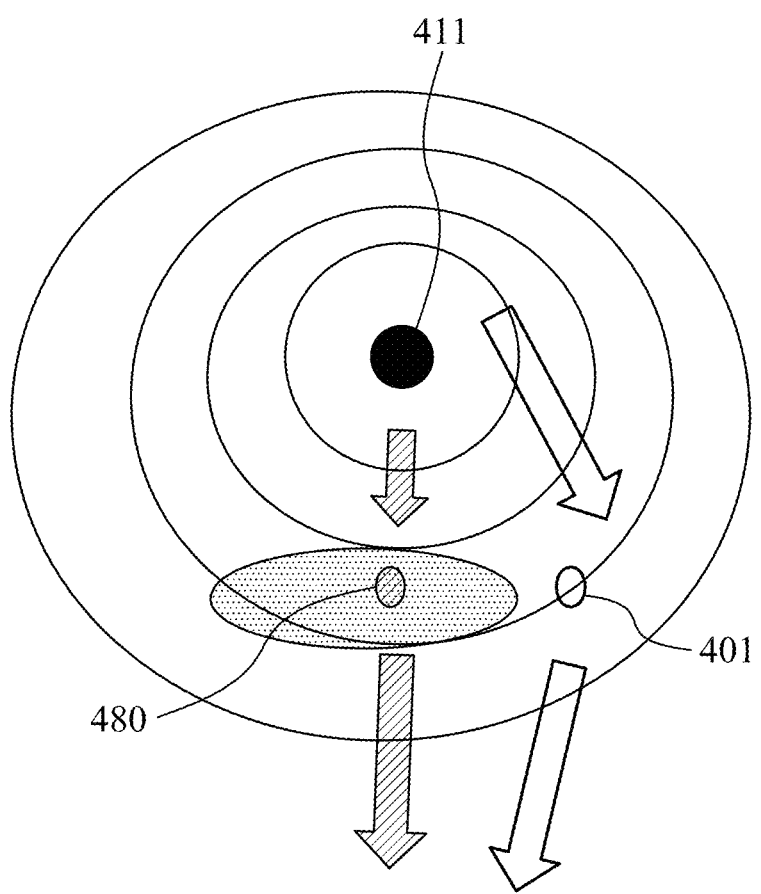
FIGS. 4E and 4F are diagrams which illustrate examples in which an influence of another reflector is eliminated by addition of received data for each channel according to an exemplary embodiment.
Figure 4F:
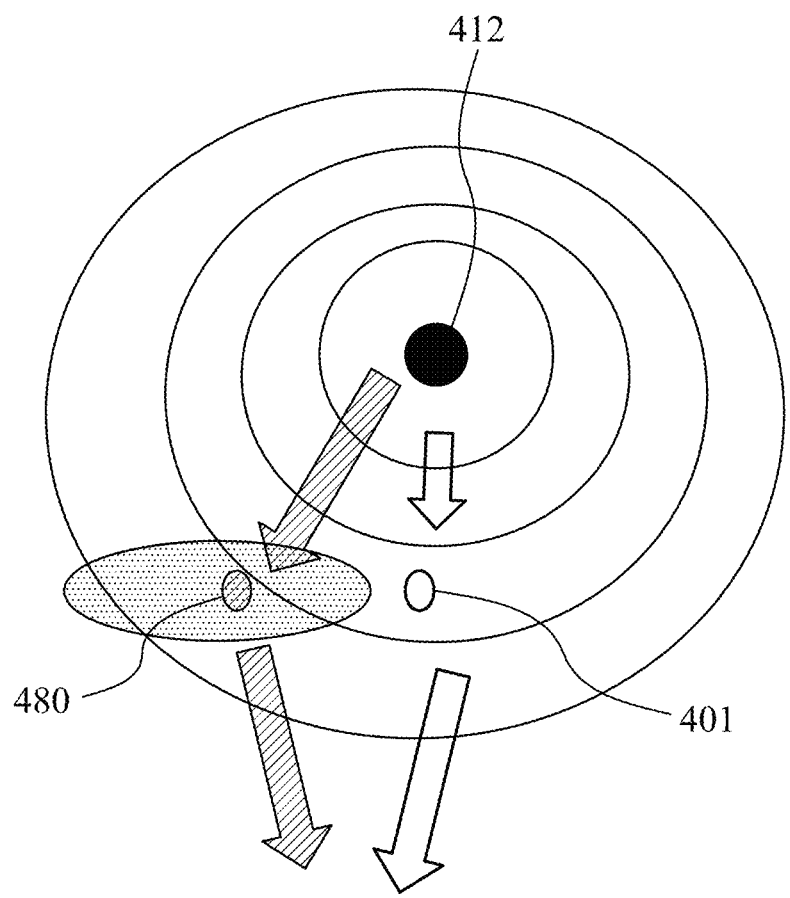

FIGS. 4E and 4F are diagrams which illustrate examples in which an influence of another reflector is eliminated by data addition for each channel according to an exemplary embodiment.

Referring to FIG. 4E, a focusing point may be a first point 411. Points in time at which a transducer receives an acoustic field from each of a first reflector 401 and a second reflector 480 may be t1 and t2, respectively. Referring to FIG. 4F, a focusing point may be determined to be a second point 412. Similarly, points in time at which a transducer receives an acoustic field from each of a first reflector 401 and a second reflector 480 may be t3 and t4, respectively. Although t1 and t2 may differ from t3 and t4, signals from another reflector in lieu of a measurement point may be cancelled out by data addition for each channel due to a difference in delay. In the example illustrated in FIG. 3, measurement time may increase because the beamfocusing is performed on multiple focusing points.

Figure 6A:
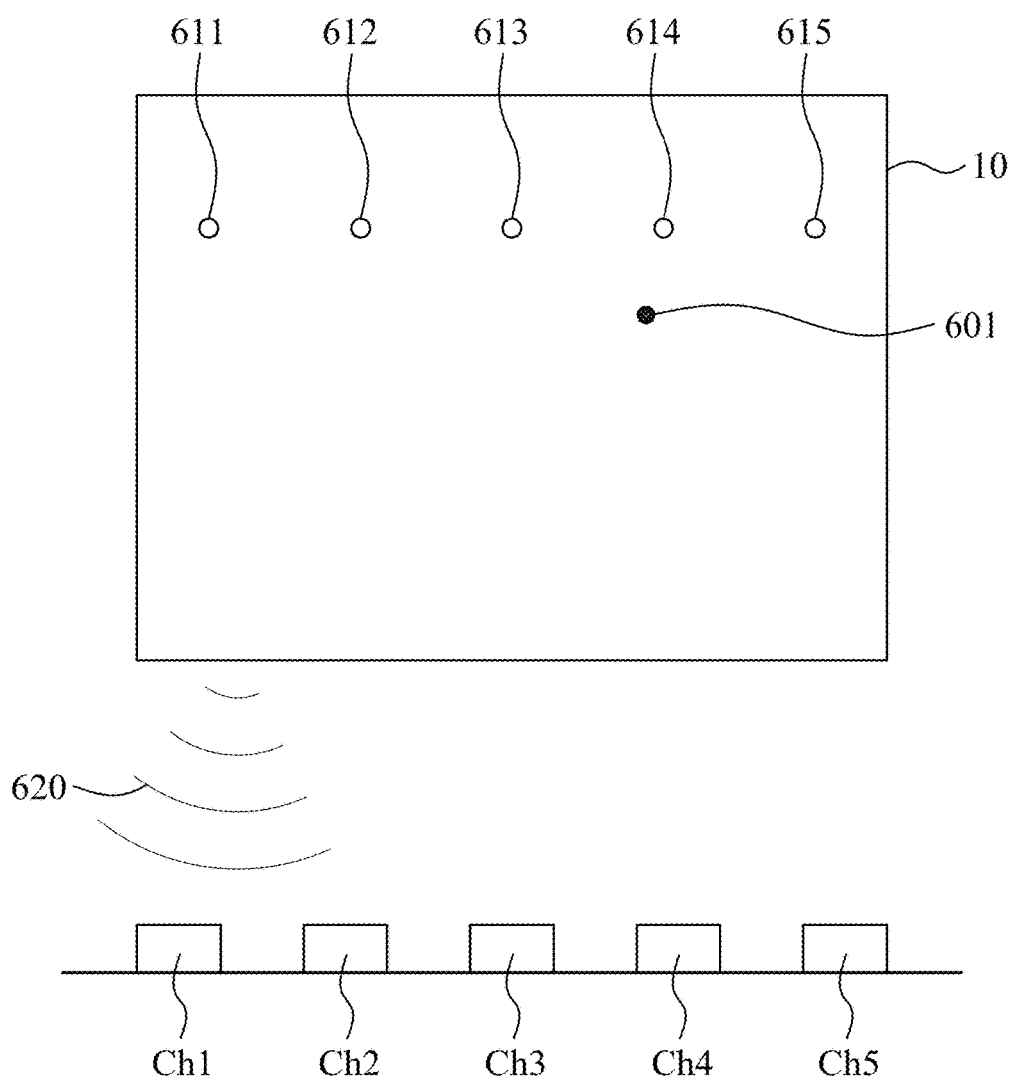
FIGS. 6A and 6B are diagrams which illustrate a beamfocusing method according to an exemplary embodiment.
Figure 6B:
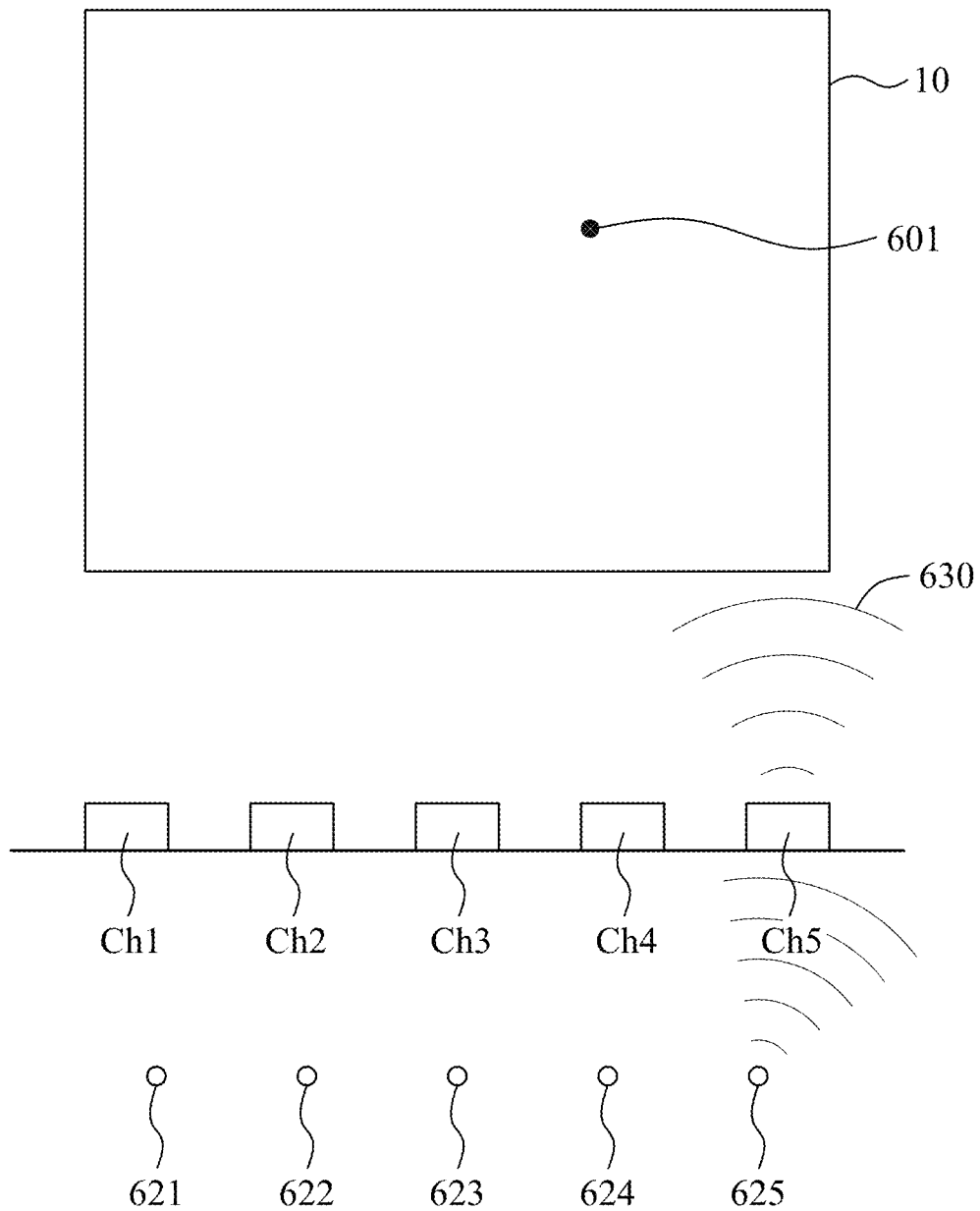

FIGS. 6A and 6B are diagrams which illustrate a beamfocusing method according to exemplary embodiments. For example, a measurement point 601 in a sample 10 is determined to be a measurement point.

Referring to FIG. 6A, an ultrasound based measurement method according to an exemplary embodiment may determine multiple focusing points, for example, 611, 612, 613, 614, and 615, in a region adjacent to the measurement point 601 and disposed farther away from the transducers than the reflector. The ultrasound based measurement method may determine the focusing points 611 through 615 in front of transducers, for example, Ch. 1 through Ch. 5, based on a front focusing method, schematically illustrated by a wave 620 for Ch. 1. The ultrasound based measurement method may determine a number of the focusing points 611 through 615 to be less than or equal to a number of the transducers Ch. 1 through Ch. 5, i.e., less than or equal to five.

Referring to FIG. 6B, an ultrasound based measurement method according to another exemplary embodiment may determine multiple focusing points, for example, 621, 622, 623, 624, and 625, in a rear of transducers, for example, Ch. 1 through Ch. 5, based on a rear focusing method, schematically illustrated by a wave 630 for Ch. 5.

Figure 7C:
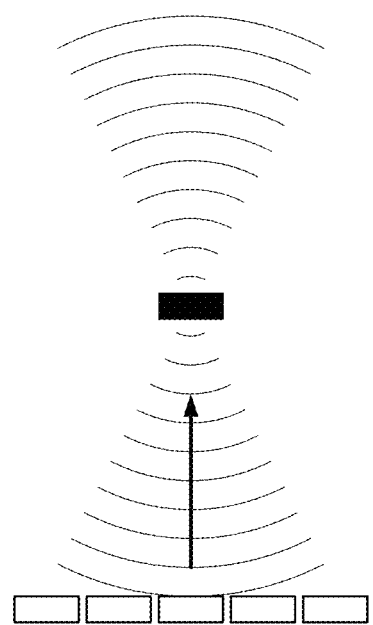

FIGS. 7A through 7C are diagrams which illustrate examples in which beamfocusing is performed on a focusing point according to an exemplary embodiment. FIG. 7A illustrates a result of performing the beamfocusing based on a scanline focusing method. FIG. 7B illustrates a result of performing the beamfocusing based on a rear focusing method. FIG. 7C illustrates a result of performing the beamfocusing based on a front focusing method.

Figure 5:
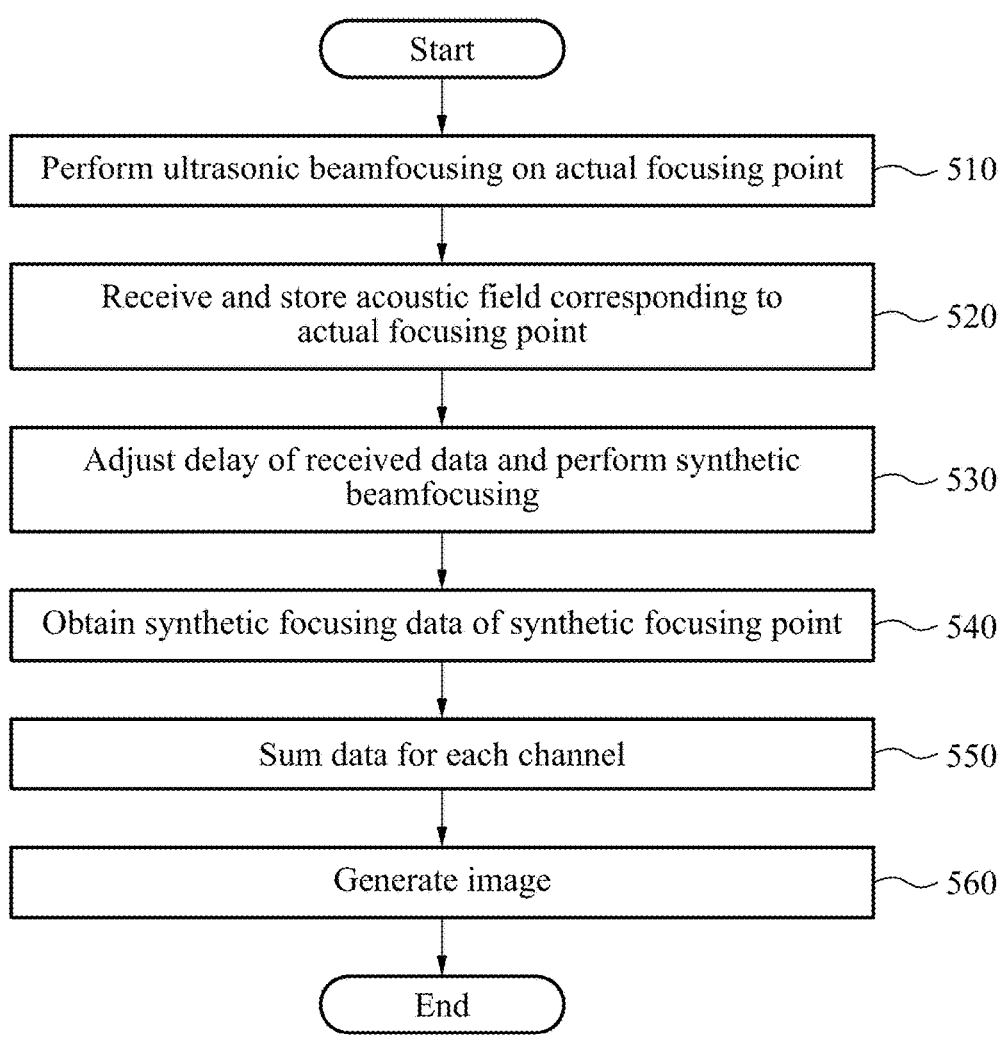
FIG. 5 is a flowchart which illustrates an ultrasound based measurement method according to an exemplary embodiment.

FIG. 5 is a flowchart which illustrates an ultrasound based measurement method in which beamfocusing is performed on at least one actual focusing point and on a plurality of synthetic focusing points, according to an exemplary embodiment.

In operation 510, the ultrasound based measurement method may perform beamfocusing on one or more of actual focusing points using an ultrasonic signal. The number of the actual focusing points may be less than or equal to a number of transducers.

In operation 520, the ultrasound based measurement method may receive and store each acoustic field corresponding to each actual focusing point.

Figure 8:
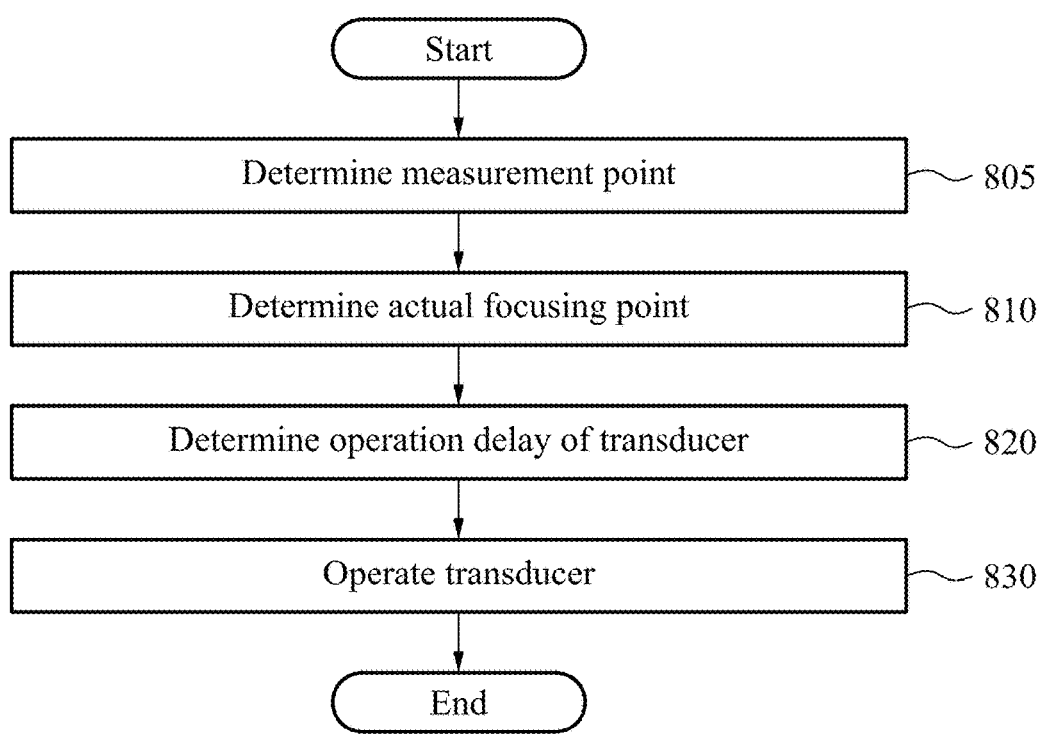
FIG. 8 is a flowchart which illustrates a beamfocusing method according to an exemplary embodiment.
Figure 9:
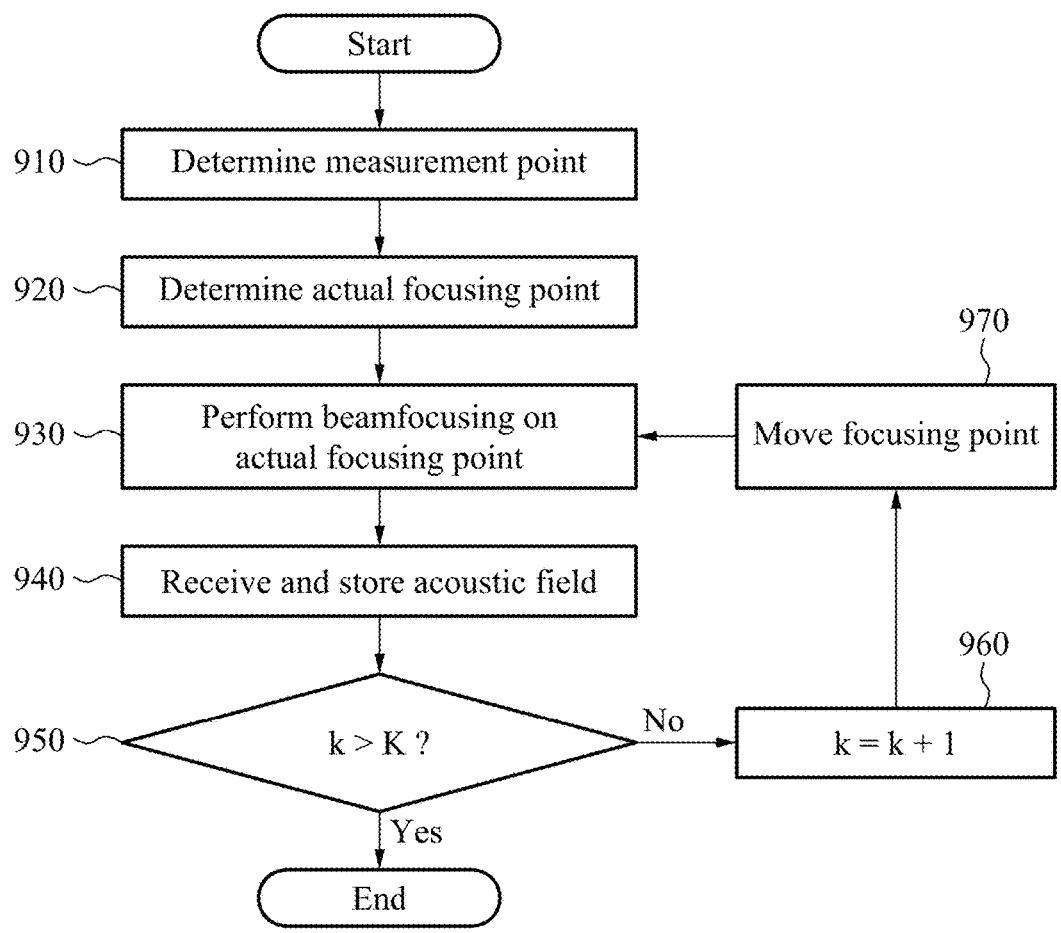
FIG. 9 is a flowchart which illustrates a beamfocusing method to be performed on multiple focusing points according to an exemplary embodiment.

FIGS. 8 and 9 are flowcharts which illustrate in detail operations 510 and 520 of a beamfocusing method of FIG. 5, according to an exemplary embodiment.

In operation 805, an ultrasound based measurement method may determine a measurement point, for example, a measurement point 601 in FIGS. 6A and 6B.

In operation 810, the beamfocusing method may determine at least one actual focusing point. In operation 820, the beamfocusing method may determine a transmission time for each transducer, or determine an operation delay between the transducers. In operation 830, the beamfocusing method may control the transducer to transmit an ultrasonic signal at the determined transmission time and accordingly, beamfocusing may be performed on an actual focusing point.

FIG. 9 is a flowchart which illustrates a beamfocusing method to be performed on multiple actual focusing points according to an exemplary embodiment.

In operation 910, an ultrasound based measurement method according to an exemplary embodiment may determine a measurement point, for example, a measurement point 601 in FIGS. 6A and 6B.

In operation 920, the ultrasound based measurement method may determine an actual focusing point. For example, the ultrasound based measurement method may determine the actual focusing point based on the front focusing method or the rear focusing method as illustrated in FIGS. 6A and 6B.

In operation 930, the ultrasound based measurement method may perform beamfocusing on a kth point, where 1≤k≤K. In operation 940, the ultrasound based measurement method may receive and store an acoustic field for each actual focusing point in response to the beamfocusing. In operation 950, the ultrasound based measurement method may compare a value of k with a value of K. When the value of k is less than or equal to the value of K, the ultrasound based measurement method may increase the value of k by 1 in operation 960, move the focusing point in operation 970 and repeat operations 930, 940, and 950. When the value of k is greater than the value of K, the operation ends.

Referring again to FIG. 5, in operation 530, the ultrasound based measurement method may adjust each delay associated with received data and perform synthetic focusing. The synthetic focusing may refer to a method of generating synthetic data corresponding to a synthetic focusing point using actually received data corresponding to an actual focusing point in a sample.

More particularly, the synthetic focusing may refer to a method of adjusting each delay associated with the received data for each channel received subsequent to the beamfocusing performed on the actual focusing point, performing the beamfocusing on the synthetic focusing point, and generating received data. For example, the ultrasound based measurement method may actually perform the beamfocusing on an actual focusing point and obtain received data corresponding to the actual focusing point. There may be a plurality of the actual focusing points and, accordingly, there may be a plurality of the actually received data sets. The ultrasound based measurement method may determine at least one of a distance and a delay between the actual focusing point on which the beamfocusing is actually performed and the synthetic focusing point on which the synthetic focusing is to be performed. For example, the ultrasound based measurement method may estimate a delay for each transducer channel based on the delay between the actual focusing point and the synthetic focusing point. The ultrasound based measurement method may adjust a delay associated with the actually received data for each channel based on the estimated delay of the transducer.

Accordingly, the ultrasound based measurement method may obtain synthetic data which may be received when the synthetic beamfocusing is performed on the synthetic focusing point. Thus, the ultrasound based measurement method may obtain the data corresponding to the synthetic focusing point without actually performing the beamfocusing on the synthetic focusing point.

In operation 540, the ultrasound based measurement method may obtain synthetic data corresponding to multiple synthetic focusing points in a region adjacent to a measurement point.

In operation 550, the ultrasound based measurement method may calculate a sum of multiple sets of the synthetic data for each channel. Although multiple reflectors may be present in a sample, an influence of an extraneous reflector other than the measurement point may be prevented or eliminated due to data addition for each channel. According to another exemplary embodiment, an ultrasound based measurement method may perform the data addition for each channel on the synthetic data and the received data.

In operation 560, the ultrasound based measurement method may generate an image of the measurement point based on the calculated sum of data for each channel. Although not illustrated, the ultrasound based measurement method may generate the image of the measurement point based on the calculated sum of data for each channel by performing aberration correction. Alternatively, the ultrasound based measurement method may extract a harmonic component from the received data and use the extracted harmonic component. For example, the ultrasound based measurement method may perform filtering or demodulation on the received data and apply receiving-end delay correction or a synthetic focusing method. More particularly, the harmonic component may be extracted by filtering the received data and generating bandpass filtered data. For example, the harmonic component may be extracted by a pulse inversion method, and converted into a baseband signal by demodulation.

Figure 10:
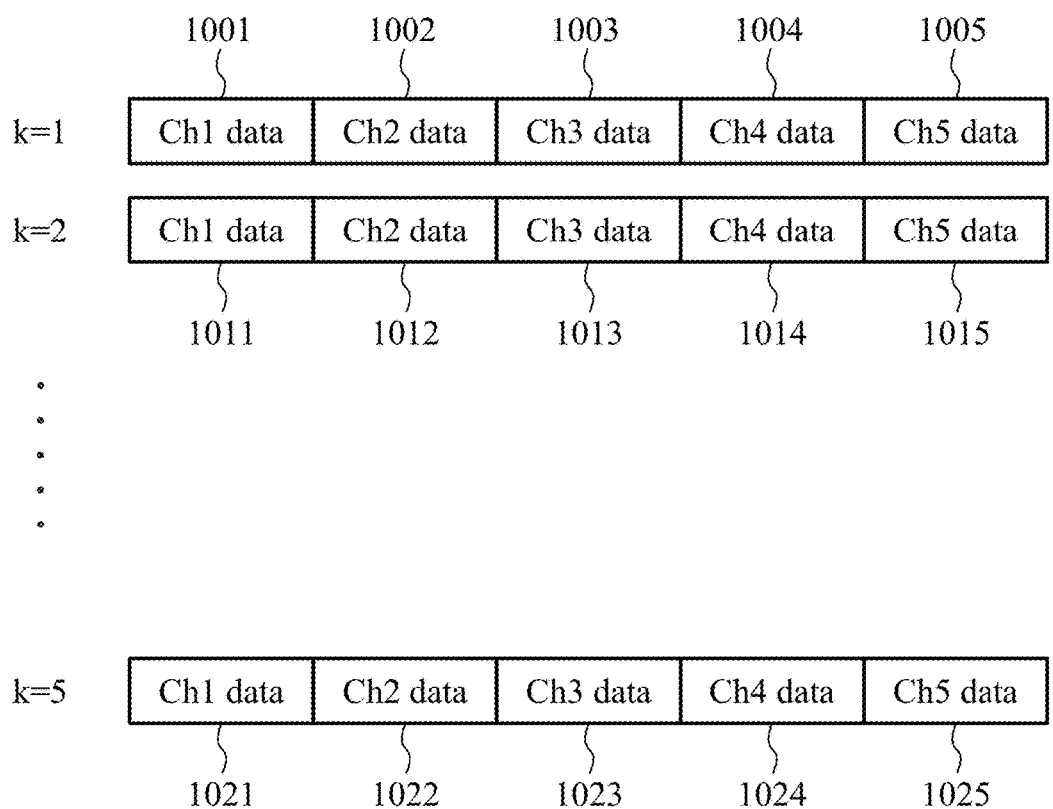
FIG. 10 is a diagram which illustrates received data associated with actual focusing according to an exemplary embodiment.

FIG. 10 is a diagram which illustrates received data associated with actual focusing according to an exemplary embodiment. The received data associated with the actual focusing may refer to data obtained when an ultrasound based measurement apparatus according to an exemplary embodiment actually transmits an ultrasonic signal to a sample and receives an acoustic field in response to the transmission of the ultrasonic signal. The received data associated with the actual focusing may include received data for each channel as illustrated in FIG. 10. The received data associated with the actual focusing may be the received data obtained by performing beamfocusing on the five focusing points 611 through 615 of FIGS. 6A and 6B. Referring to FIG. 10, first received data as a result of the beamfocusing performed on the first point 611 may include first channel first received data 1001, second channel first received data 1002, third channel first received data 1003, fourth channel first received data 1004, and fifth channel first received data 1005. Second received data as a result of the beamfocusing performed on the second point 612 may include first channel second received data 1011, second channel second received data 1012, third channel second received data 1013, fourth channel second received data 1014, and fifth channel second received data 1015. Fifth received data as a result of the beamfocusing performed on the fifth point 615 may include first channel fifth received data 1021, second channel fifth received data 1022, third channel fifth received data 1023, fourth channel fifth received data 1024, and fifth channel fifth received data 1025.

Figure 11A:
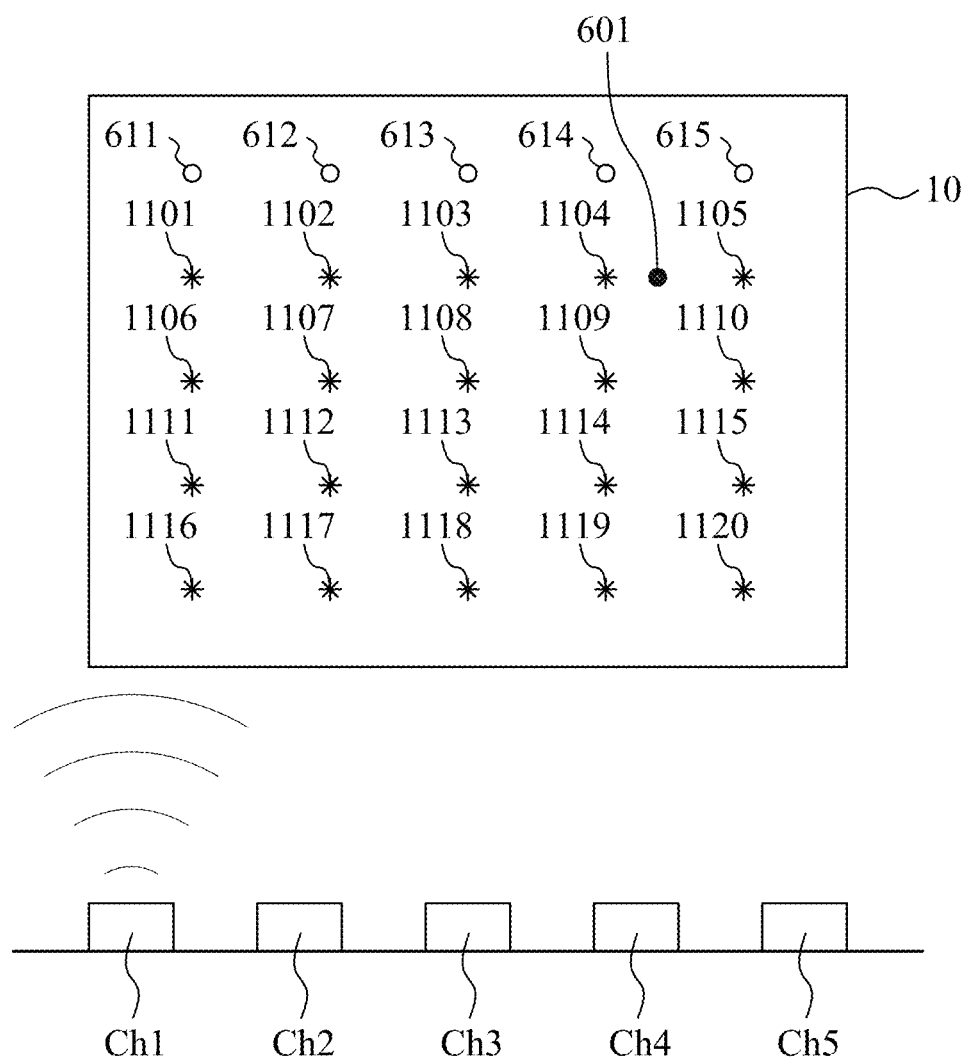
FIGS. 11A and 11B are diagrams which illustrate a synthetic focusing point in a sample according to an exemplary embodiment.
Figure 11B:
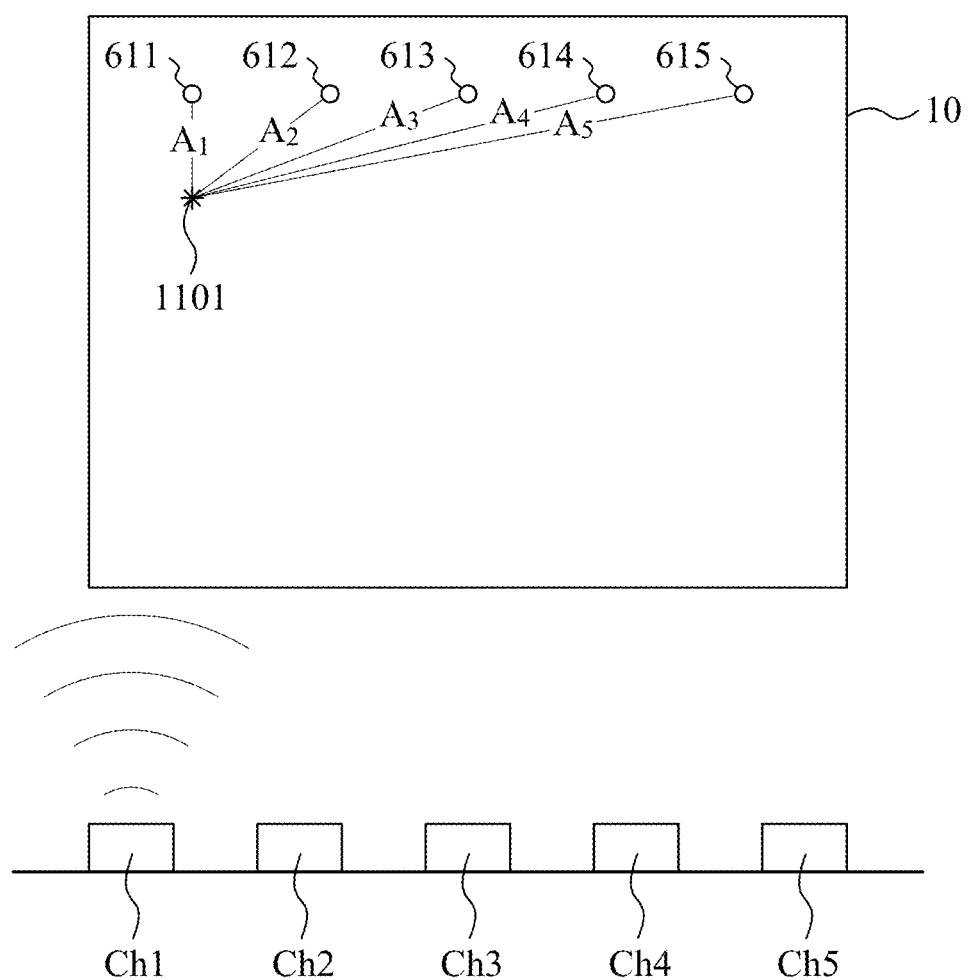

FIGS. 11A and 11B are diagrams which illustrate a synthetic focusing point in a sample according to an exemplary embodiment. More detailed descriptions of FIGS. 11A and 11B will be provided with reference to FIG. 12.

Figure 12:
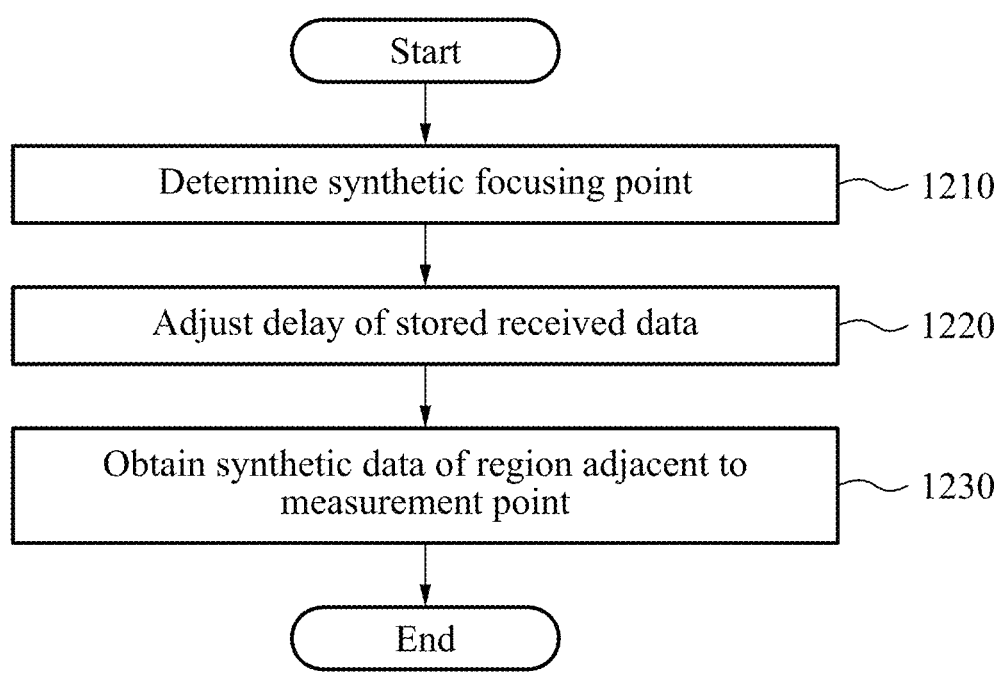
FIG. 12 is a flowchart which illustrates an example of a method of obtaining synthetic data according to an exemplary embodiment.

Referring to FIG. 12, in operation 1210, an ultrasound based measurement method according to an exemplary embodiment may determine a synthetic focusing point. For example, the ultrasound based measurement method may determine multiple synthetic focusing points, for example, 1101, 1102, 1103, 1104, 1105, 1106, 1107, 1108, 1109, 1110, 1111, 1112, 1113, 1114, 1115, 1116, 1117, 1118, 1119, and 1120, as illustrated in FIG. 11A. The ultrasound based measurement method may determine the synthetic focusing points 1101 through 1120 in a region adjacent to a measurement point 601 of FIG. 11A. For example, the ultrasound based measurement method may determine the synthetic focusing points 1101 through 1120 so that they are separated from one another at predetermined intervals and are disposed in an overall form of a rectangular grid, with a measurement point 601 disposed within the grid or outside of the grid.

In operation 1220, the ultrasound based measurement method may adjust a delay associated with stored received data of the actual focusing points to obtain received data corresponding to each of the synthetic focusing points 1101 through 1120. In operation 1230, the ultrasound based measurement method may obtain the synthetic data of the region adjacent to the measurement point 601. For example, the ultrasound based measurement method as illustrated in FIG. 11B may obtain delays, for example, A1, A2, A3, A4, and A5, between actual focusing points 611 through 615 and a synthetic focusing point 1101. The ultrasound based measurement method may perform a synthetic focusing method based on the delay obtained between the synthetic focusing point 1101 and the actual focusing points 611 through 615 and a delay for each transducer.

The synthetic data corresponding to the synthetic focusing point 1101 may be obtained based on the received data associated with the actual focusing as illustrated in FIG. 10. For example, a focusing period of time from the transducer to the actual focusing points 611 through 615 may be indicated as t1, and the delays between each of the actual focusing points 611 through 615 and the synthetic focusing point 1101 may be correspondingly indicated as A1, A2, A3, A4, and A5.

The ultrasound based measurement method may apply t1−A1 delay to the received data corresponding to the first actual focusing point. For example, the ultrasound based measurement method may apply t1−A2 delay through t1−A5 delay to the received data corresponding to the second actual focusing point through the fifth actual focusing point. The ultrasound based measurement method may sum all the received data corresponding to the first actual focusing point through the fifth actual focusing point to which the delay is applied, and obtain the synthetic data corresponding to the synthetic focusing point 1101.

The t1−A1 delay may be provided as an example that may be applicable when the synthetic focusing point 1101 is closer to the transducer in comparison to the actual focusing points 611 through 615. When the actual focusing points 611 through 615 are closer to the transducer in comparison to the synthetic focusing point 1101, a delay may be determined to be t1+A1.

As described above, the ultrasound based measurement method may obtain the synthetic data and accordingly, obtain data identical or substantially similar to the received data associated with the actual focusing, as illustrated in FIG. 4C. The ultrasound based measurement method may apply the synthetic focusing method to the received data and obtain the received data, as illustrated in FIG. 4C, without performing the actual focusing, as illustrated in FIG. 4B. According to an exemplary embodiment, the ultrasound based measurement method may obtain the received data sets based on a relatively great overall number of focusing points in a region adjacent to the measurement point using the synthetic focusing method by performing the beamfocusing on a relatively fewer number of actual focusing points, than the overall number of focusing points. Accordingly, an amount of time for calculation and measurement may be substantially reduced.

Figure 13:
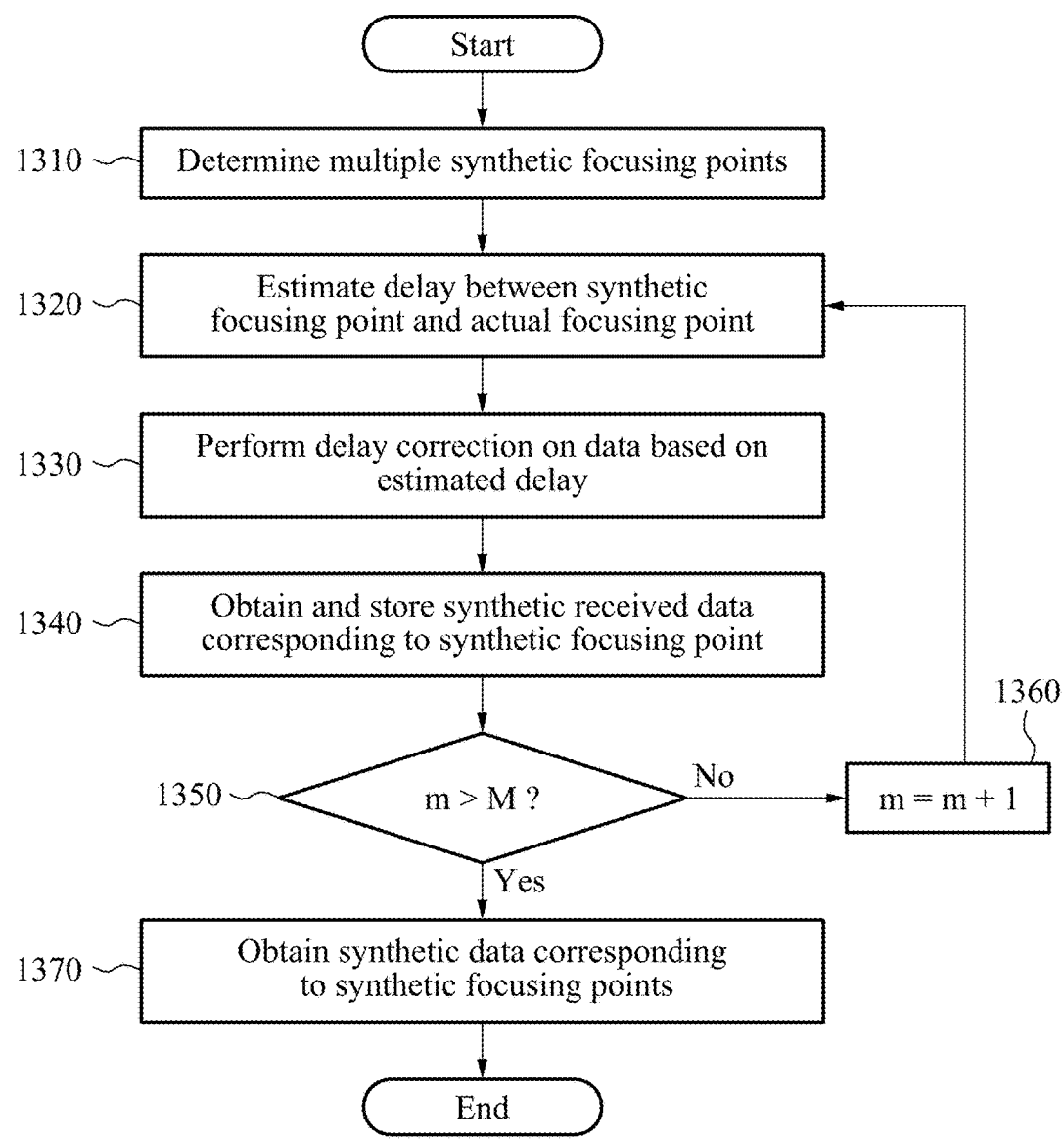
FIG. 13 is a flowchart which illustrates another example of a method of obtaining synthetic data according to an exemplary embodiment.

FIG. 13 is a flowchart which illustrates an example of a method of obtaining synthetic data according to an exemplary embodiment. For example, an ultrasound based measurement method to be described with reference to FIG. 13 may store received data from an actual focusing point.

In operation 1310, the ultrasound based measurement method may determine M synthetic focusing points, for example, in a region adjacent to a measurement point.

In operation 1320, the ultrasound based measurement method may estimate a delay and/or a distance between a synthetic focusing point and the actual focusing point. A number of synthetic focusing points may be from 1 to M. The ultrasound based measurement method may also estimate a delay for each transducer channel based on a difference between a measurement time from the synthetic focusing point to the transducer and a measurement time from the actual focusing point to the transducer. Accordingly, the delay for each transducer may be estimated.

In operation 1330, the ultrasound based measurement method may perform delay correction on the received data based on the estimated delay. In operation 1340, the ultrasound based measurement method may obtain and store the synthetic data corresponding to the synthetic focusing point.

In operation 1350, the ultrasound based measurement method may determine that a value of m is less than or equal to a value of M. In operation 1360, a value of m may be increased by 1 and the ultrasound based measurement method may return to operation 1320. The ultrasound based measurement method may perform the foregoing operations repeatedly until a value of m exceeds a value of M. When the value of m is greater than the value of M, the operation ends.

In operation 1370, the ultrasound based measurement method may obtain the synthetic data corresponding to synthetic focusing points in the region adjacent the measurement point.

Figure 14:
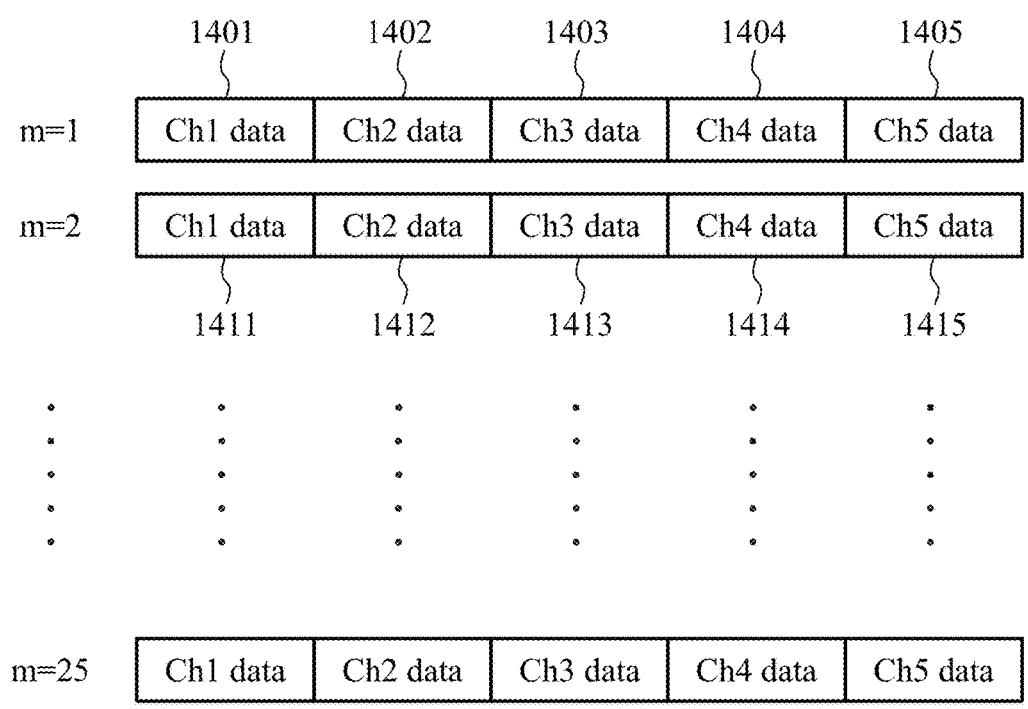
FIG. 14 is a diagram which illustrates an example of synthetic data according to an exemplary embodiment.

FIG. 14 is a diagram which illustrates an example of synthetic data according to an exemplary embodiment.

Figure 15:
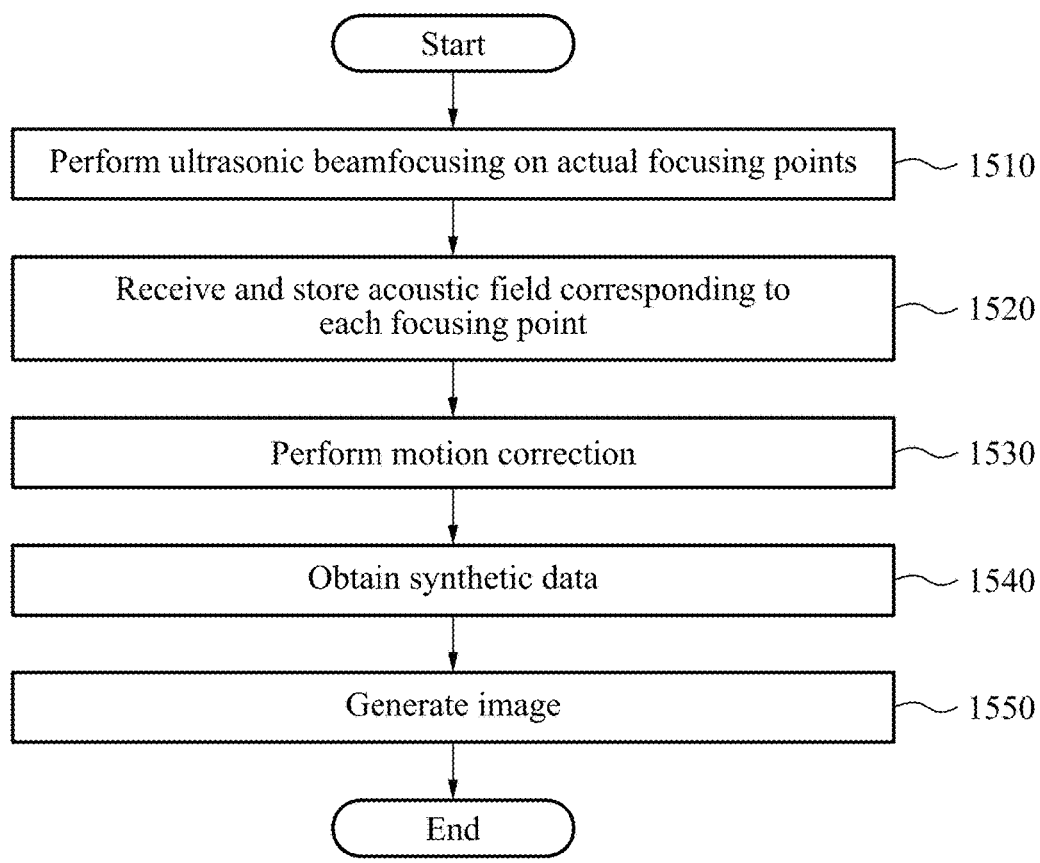
FIG. 15 is a flowchart which illustrates an ultrasound based measurement method that corrects a motion of a reflector according to an exemplary embodiment.

Referring to FIG. 14, a number of sets of the synthetic data may be 25 and each set of the synthetic data may include data for each channel. For example, first synthetic data may include first channel first synthetic data 1401, second channel first synthetic data 1402, third channel first synthetic data 1403, fourth channel first synthetic data 1404, and fifth channel first synthetic data 1405; second synthetic data may include first channel second synthetic data 1411, second channel second synthetic data 1412, third channel second synthetic data 1413, fourth channel second synthetic data 1414, and fifth channel second synthetic data 1415; etc. The synthetic data of FIG. 14 may include actually received data. For example, an ultrasound based measurement method according to an exemplary embodiment may generate 25 sets of the received data by generating five sets of the actually received data and 20 sets of the synthetic data. As another example, the ultrasound based measurement method may generate 25 sets of the received data by generating 25 sets of the synthetic data based on 5 sets of the actual received data. However, the above examples are not limiting and the ultrasound based measurement method may generate any number of sets of the received data in any other appropriate manner. FIG. 15 is a flowchart which illustrates an example of an ultrasound based measurement method that may correct a motion of a reflector when the reflector moves in a sample, according to an exemplary embodiment.

In operation 1510, the ultrasound based measurement method may perform ultrasonic beamfocusing on actual focusing points using an ultrasonic signal. For example, the ultrasound based measurement may perform the ultrasonic beamfocusing based on a front focusing method or a rear focusing method as illustrated in FIGS. 6A and 6B. The ultrasound based measurement method may perform receiving-end beamfocusing on the multiple points in a sample by transmitting the ultrasonic signal from a plurality of transducers. The ultrasound based measurement method may perform the ultrasonic beamfocusing on a number of focusing points less than a number of the transducers.

In operation 1520, the ultrasound based measurement method may receive an acoustic field in response to the ultrasonic beamfocusing performed on each of the multiple points in the sample. The ultrasound based measurement method may receive the acoustic field, and obtain and store received data. The received data may include data for each channel of the transducers and be measured for a predetermined duration.

In operation 1530, the ultrasound based measurement method may perform motion correction on the data for each channel. More particularly, the ultrasound based measurement method may generate image frames based on an elapsed time. The ultrasound based measurement method may detect the motion of the reflector by a comparison of neighboring image frames. The ultrasound based measurement method may estimate a delay between a location of the reflector prior to the motion and a location of the reflector subsequent to the motion. The ultrasound based measurement method may perform the motion correction by correcting the data for each channel based on the estimated delay. Detection of a motion vector may be performed by a display, although the correction of the motion may be performed by adjusting the delay associated with the data for each channel.

In operation 1540, the ultrasound based measurement method may obtain the synthetic data, as described above. For example, the ultrasound based measurement method may determine a synthetic focusing point and estimate a delay between the synthetic focusing point and an actual focusing point. The ultrasound based measurement method may correct the data for each channel based on the delay between the synthetic focusing point and the actual focusing point and accordingly, the synthetic data corresponding to the synthetic focusing point may be obtained.

In operation 1550, the ultrasound based measurement method may generate an image based on the synthetic data and the received data associated with actual focusing. The ultrasound based measurement method may calculate a sum of the data for each channel. According to above-described exemplary embodiments, an influence of an extraneous reflector other than a measurement point may be prevented. The ultrasound based measurement method may perform aberration correction and generate the image based on the summed data on which the aberration correction is performed.

The ultrasound based measurement method may recalculate a delay error by applying the synthetic focusing or the motion correction. Also, the ultrasound based measurement method may control the foregoing operations to be repeatedly performed by re-executing the synthetic focusing.

Figure 16:
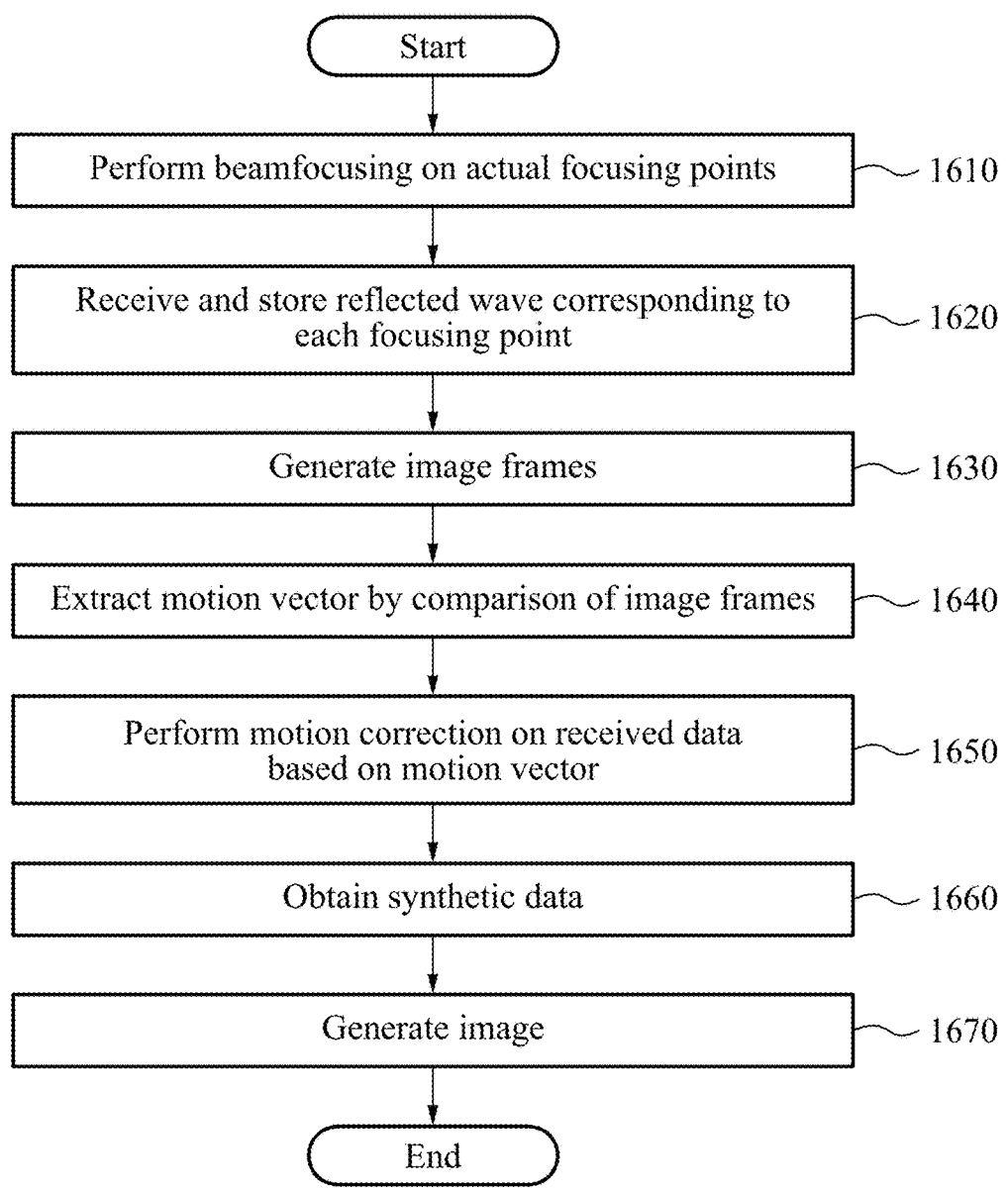
FIG. 16 is a flowchart which illustrates an ultrasound based measurement method that performs motion correction according to an exemplary embodiment.
Figure 17A:
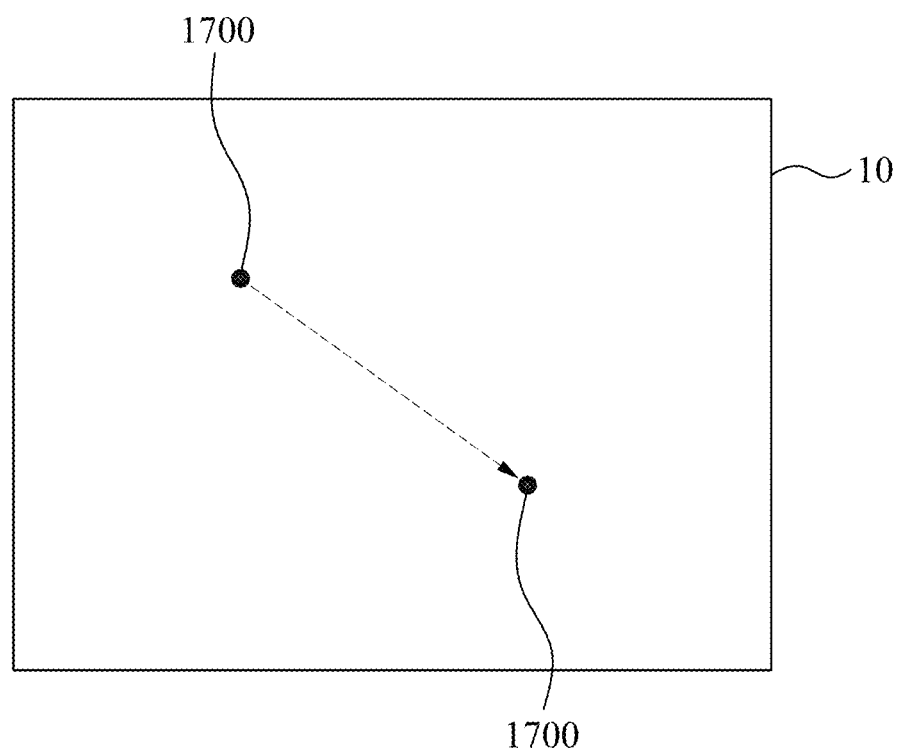
FIG. 17A is a diagram which illustrates a motion of a reflector in a sample according to an exemplary embodiment.

FIG. 16 is a flowchart which illustrates an ultrasound based measurement method that performs motion correction according to an exemplary embodiment. A method of performing the motion correction will be further described with reference to FIGS. 17A through 17C and 18. In FIG. 16, it is assumed that a reflector 1700 moves in a sample 10 as illustrated in FIG. 17A.

In operation 1610, the ultrasound based measurement method may perform ultrasonic beamfocusing on actual focusing points in the sample 10. For example, the ultrasound based measurement method may perform the beamfocusing based on a front focusing method or a rear focusing method as illustrated in FIGS. 6A and 6B.

In operation 1620, the ultrasound based measurement method may receive an acoustic field in response to the beamfocusing performed on each focusing point in the sample 10, and obtain and store received data. The received data may include data for each channel of transducers and be measured for a predetermined duration.

In operation 1630, the ultrasound based measurement method may generate an image frame based on the received data. As described above, the received data may be measured for the predetermined duration and stored based on a period of time elapsing. The ultrasound based measurement method may generate multiple image frames for the predetermined duration based on the received data stored based a period of time elapsing. For example, the ultrasound based measurement method may generate a first image frame 1710, a second image frame 1720, and a third image frame 1730 as illustrated in FIG. 17B. The ultrasound based measurement method may detect a motion of a reflector based on the first image frame 1710, the second image frame 1720, and/or the third image frame 1730. For example, the ultrasound based measurement method may determine motion if a distance between a reflector 1711 in the first image frame 1710 and a reflector 1721 in the second image frame 1720 is greater than or equal to a threshold.

In operation 1640, the ultrasound based measurement method may extract a motion vector by comparing a distance between locations of reflectors in neighboring image frames with the threshold. For example, the ultrasound based measurement method may verify the motion by comparing a reflector 1731 in the third image frame 1730 to the reflector 1711 in the first image frame 1710. For example, the ultrasound based measurement method may compare the third image frame 1730 to the second image frame 1720 and determine that the motion vector is "0." Accordingly, the ultrasound based measurement method may verify that a motion vector between a location of the reflector 1731 in the third image frame 1730 and a location of the reflector 1711 in the first image frame 1710 is identical to a motion vector between a location of the reflector 1721 in the second image frame 1720 and the location of the reflector 1711 in the first image frame 1710.

Although not illustrated, a reflector may move again in a fourth image frame. The ultrasound based measurement method may detect a motion vector by comparing the reflector in the fourth image frame to the reflector 1731 in the third image frame 1730. The ultrasound based measurement method may obtain a motion vector between the reflector in the fourth image frame and a reflector in an initial image frame. More particularly, the ultrasound based measurement method may obtain the motion vector (Δ) between the fourth frame and the first frame by adding the motion vector between the third frame and the first frame together with the motion vector between the fourth frame and the third frame.

Figure 17C:
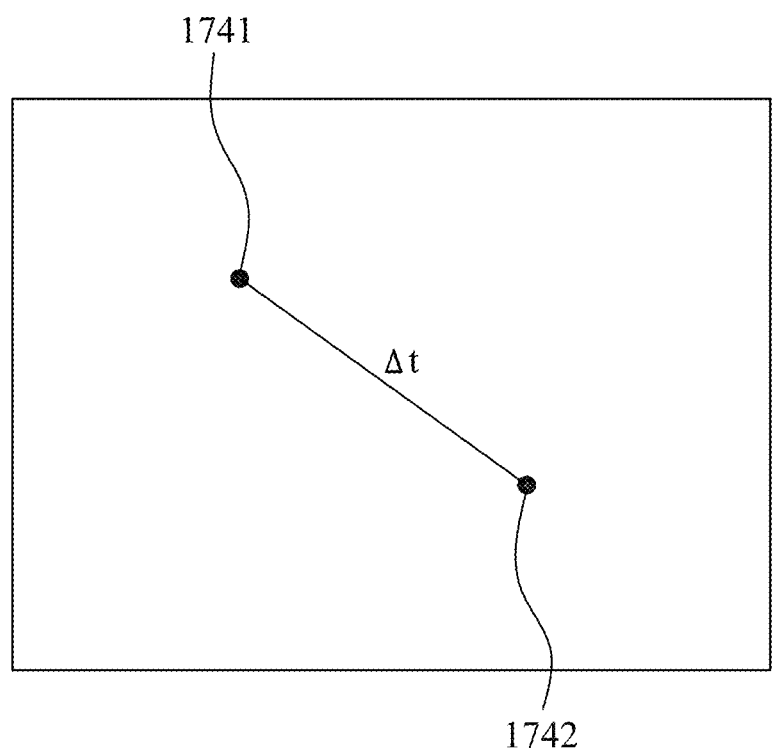
FIG. 17C is a diagram which illustrates a process of detecting a motion vector and correcting a delay according to an exemplary embodiment.

In operation 1650, the ultrasound based measurement method may correct a motion of the received data based on the motion vector. For example, as illustrated in FIG. 17C, the ultrasound based measurement method may estimate a delay (Δt) between a point 1741 corresponding to the location of the reflector 1711 in the first image frame 1710, i.e., prior to the motion, and a point 1742 corresponding to the location of the reflector 1721 in the second image frame 1720, i.e., subsequent to the motion. The ultrasound based measurement method may estimate a delay for each channel of the transducers based on the delay Δt between the point 1741 and the point 1742. The ultrasound based measurement method may perform delay correction on the received data for each channel, based on the estimated delay for each channel of the transducers. Accordingly, the motion correction may be performed on the received data.

Figure 18:
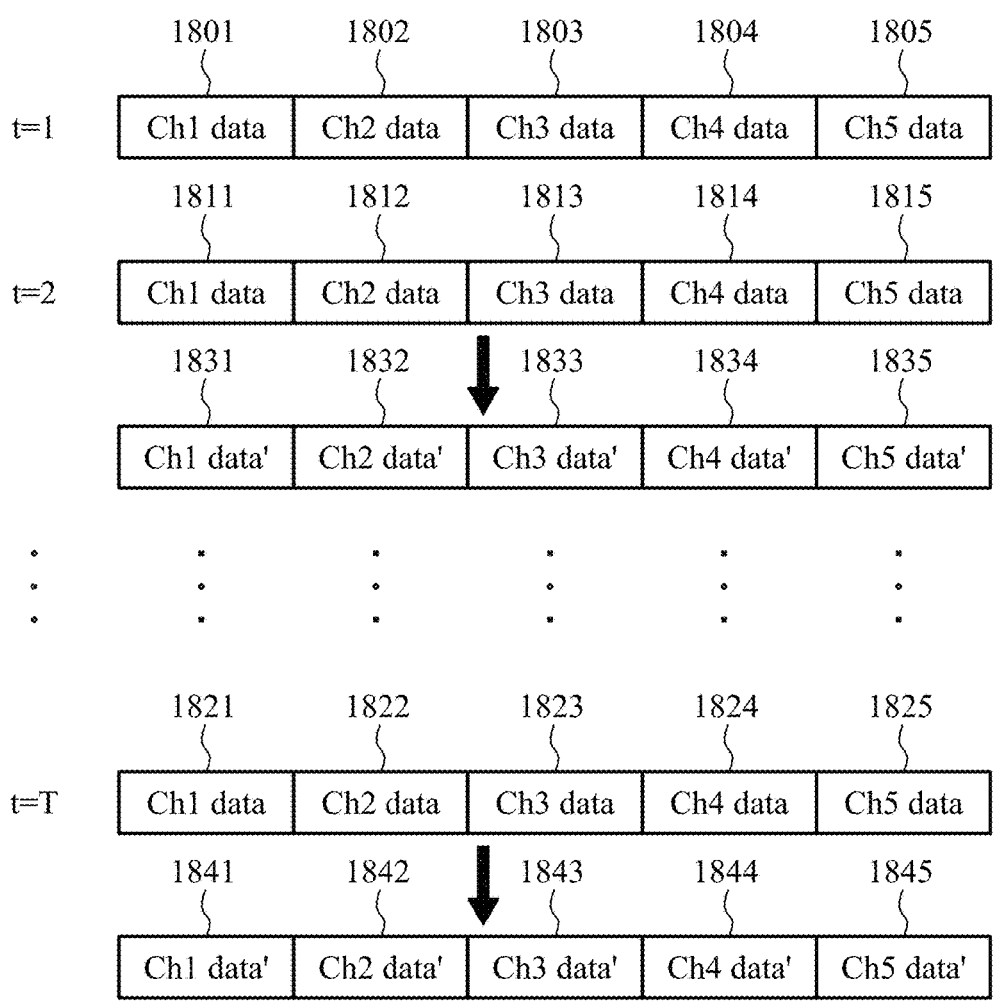
FIG. 18 is a diagram which illustrates motion correction according to an exemplary embodiment.

FIG. 18 is a diagram which illustrates motion correction performed on received data according to an exemplary embodiment.

Referring to FIG. 18, the received data may be obtained in response to beamfocusing performed on a first point. The received data may be stored when a value of t is 1, 2, . . . , T. Here, t may be a time index of a sampling section. For example, the received data in each period of time may include data for each channel. For example, when the value of t is 1, the received data may include first channel received data through fifth channel received data, for example, first data sets 1801, 1802, 1803, 1804, and 1805. When the value of t is 2, the received data may include first channel received data through fifth channel received data, for example, second data sets 1811, 1812, 18, 13, 1814, and 1815. When the value of t is T, the received data may include first channel received data through fifth channel received data, for example, third data sets 1821, 1822, 1823, 1824, and 1825.

As another example, a reflector may move between a first sampling section and a second sampling section, i.e., between the first frame 1710 and the second frame 1720, as illustrated in FIG. 17B. Here, it is assumed that the reflector remains stationary between a section subsequent to the second sampling section and a Tth sampling section. In this case, an ultrasound based measurement method according to an exemplary embodiment may perform delay correction, for each channel, on the received data corresponding to the second sampling section through the Tth sampling section. More particularly, the ultrasound based measurement method may estimate a delay for each channel in each sampling section, and perform the delay correction for each channel based on the estimated delay for each channel. Accordingly, the ultrasound based measurement method may correct the received data corresponding to the second sampling section through the received data corresponding to the Tth sampling section to be identical to the received data indicating that the reflector is positioned stationary at an initial location, i.e., as in the first sampling section.

For example, the ultrasound based measurement method may correct the received data indicating that a reflector 1700 illustrated in FIG. 17A is positioned continuously at the initial location.

As illustrated in FIG. 18, the ultrasound based measurement method may generate first corrected sets of received data, for example, 1831, 1832, 1833, 1834, and 1835, obtained by performing the motion correction on the data for each channel in the second sampling section, and second corrected sets of received data, for example, 1841, 1842, 1843, 1844, and 1845, obtained by performing the motion correction on the data for each channel in the Tth sampling section. Here, it is understood that the motion correction may also be performed on the received data in the sampling sections between the second sampling section and the Tth sampling section.

Referring again to FIG. 16, in operation 1660, the ultrasound based measurement method may obtain synthetic data based on the received data on which the motion is corrected. In operation 1670, the ultrasound based measurement method may generate an image based on the synthetic data. The ultrasound based measurement method may calculate a sum of data for each channel. According to exemplary embodiments, an influence of another reflector other than a measurement point may be prevented. The ultrasound based measurement method may perform aberration correction. The ultrasound based measurement method may generate the image based on the summed data on which the aberration correction is performed.

According to exemplary embodiments, although a moving reflector is present in a sample, a clearer image may be generated based on the motion correction.

Figure 19:
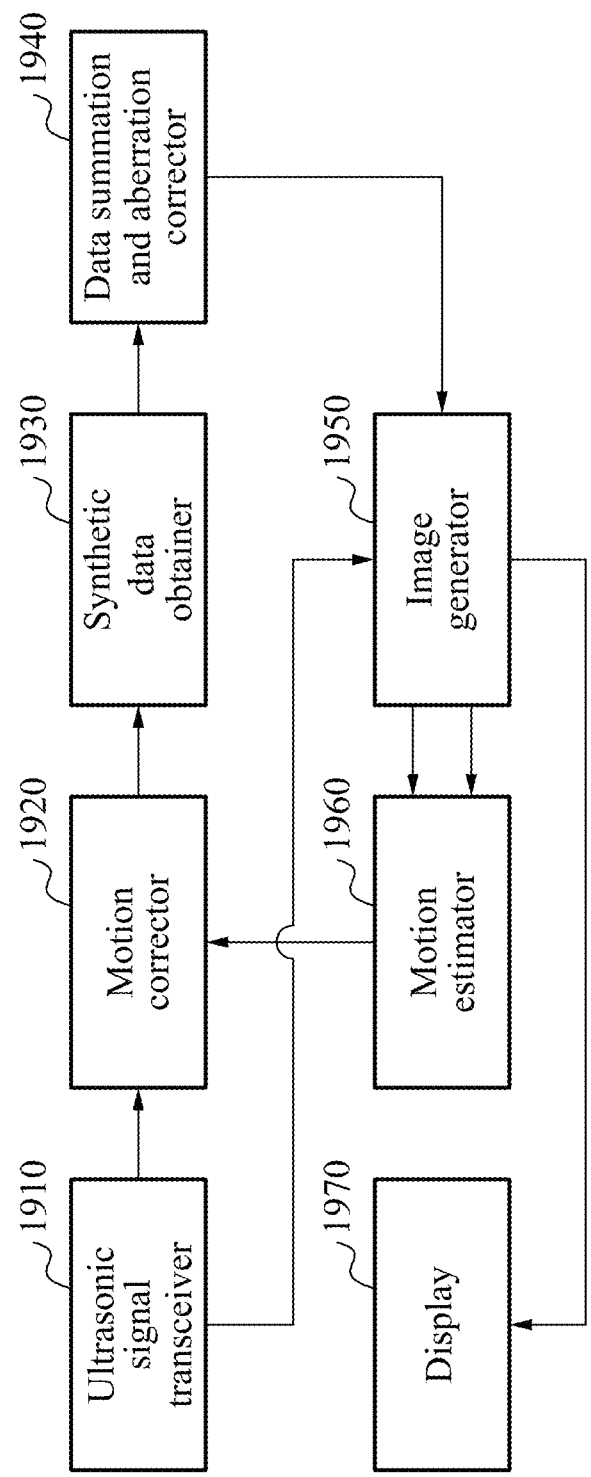
FIG. 19 is a diagram which illustrates an ultrasound based measurement apparatus that performs motion correction according to an exemplary embodiment.

FIG. 19 is a diagram which illustrates an ultrasound based measurement apparatus that performs motion correction according to an exemplary embodiment.

Referring to FIG. 19, the ultrasound based measurement apparatus may include an ultrasonic signal transceiver 1910, a motion corrector 1920, a synthetic data obtainer 1930, a data addition and aberration corrector 1940, an image generator 1950, a motion estimator 1960, and a display 1970.

The ultrasonic signal transceiver 1910 may transmit an ultrasonic signal to at least one actual focusing point in a sample, and receive an acoustic field generated by a reflector in response to ultrasonic beamfocusing.

The image generator 1950 may generate image frames based on received data corresponding to the received acoustic field. The received data may be time series data. For example, the received data may include sampling numbers and data for each transducer channel as indicated in Table 1. Thus, the image generator 1950 may generate the image frames based on a lapse of time.

The motion corrector 1920 may correct a moving reflector based on a comparison of the generated image frames. The motion corrector 1920 may correct, for each channel, a motion of the received data based on a motion vector estimated by the motion estimator 1960.

The synthetic data obtainer 1930 may apply a synthetic focusing method to the received data in which the motion is corrected. Thus, the synthetic data obtainer 1930 may obtain at least one set of synthetic data.

The data addition and aberration corrector 1940 may obtain single channel data by calculating a sum of the sets of synthetic data for each channel. The data addition and aberration corrector 1940 may perform aberration correction on the single channel data.

The image generator 1950 may generate an image based on the single channel data on which the aberration correction is performed. The display 1970 may display the generated image.

Figure 20A:
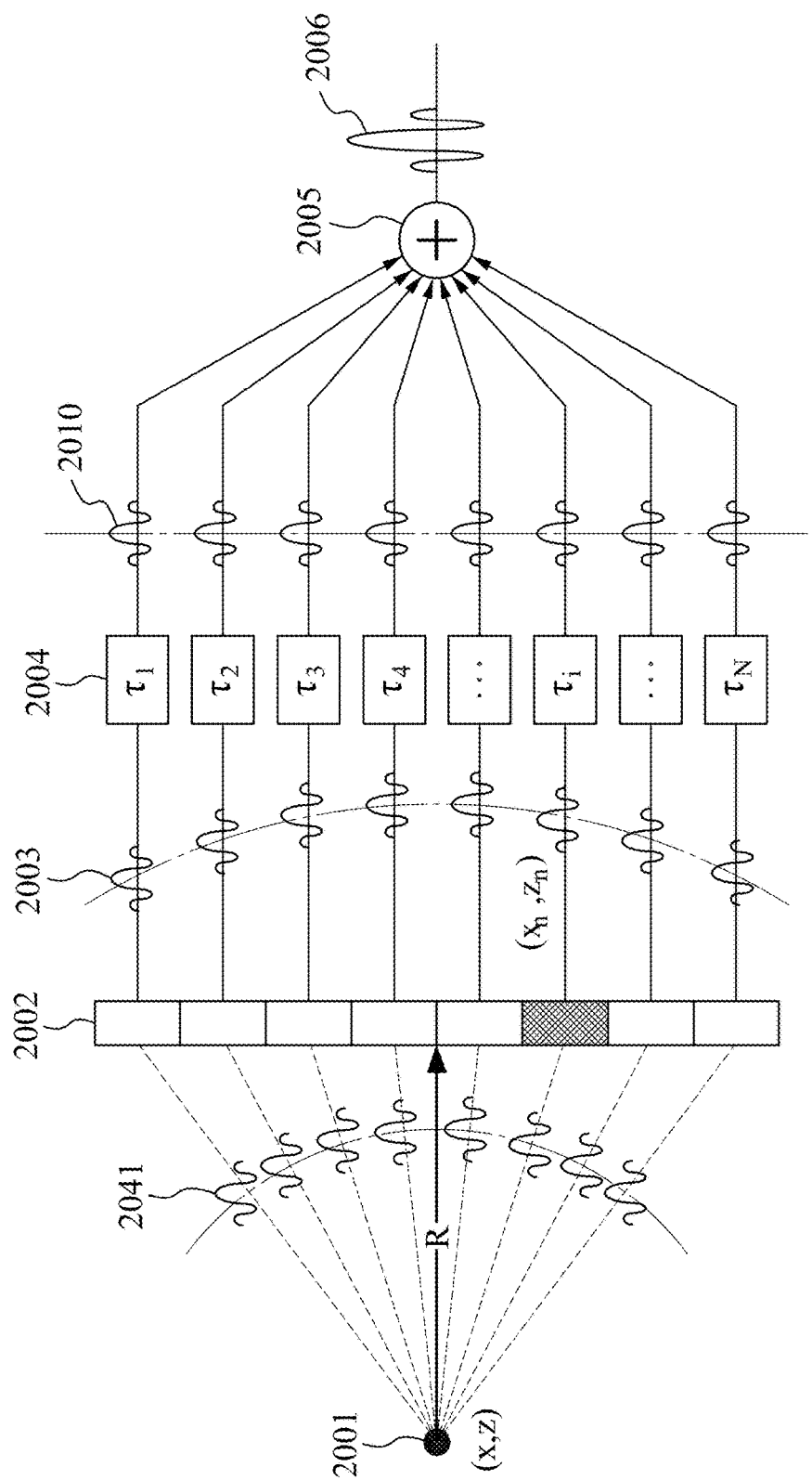
FIGS. 20A, 20B and 20C are diagrams which illustrate a process of aberration correction according to an exemplary embodiment.
Figure 20B:
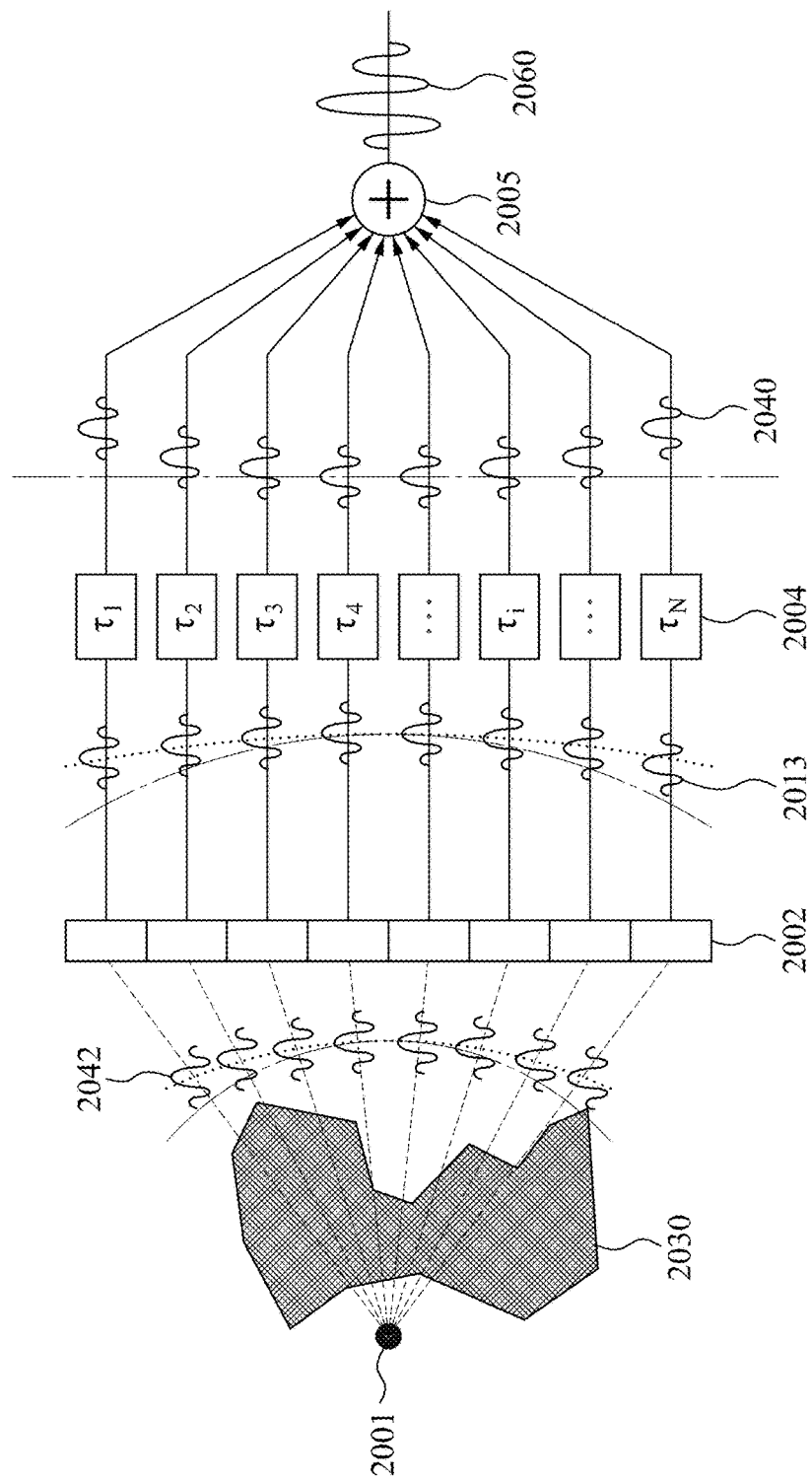

FIGS. 20A and 20B are diagrams which illustrate a process of aberration correction according to an exemplary embodiment.

Referring to FIG. 20A, a reflector 2001 having coordinates (x, z) may reflect an acoustic field 2041. The reflector 2001 may be separated by a distance R from a central point of a transducer array 2002. The acoustic field 2041 may be a spherical wave and accordingly, a point in time at which the acoustic field 2041 arrives at each transducer may be different. Transducers of the transducer array 2002 may convert the received acoustic field 2041 into first electrical signals 2003 and output the first electrical signals 2003. An aberration corrector 2004 may adjust delays of the received first electrical signals 2003, in correspondence with the transducers, and output second electrical signals 2010 obtained by aberration correction. A signal adder 2005 may sum the second electrical signals 2010 obtained by the aberration correction and generate an image signal 2006.

Referring to FIG. 20B, in a medium 2030 having an irregular speed of sound, an acoustic field 2042 may arrive at each transducer at irregular points in time, departing from a form of a spherical wave. Although the aberration corrector 2004 performs the aberration correction on converted first electrical signals 2013, a delay may occur between second electrical signals 2040 obtained by the aberration correction. Accordingly, an image signal 2060 may be distorted with respect to the reflector 2001.

Figure 20C:
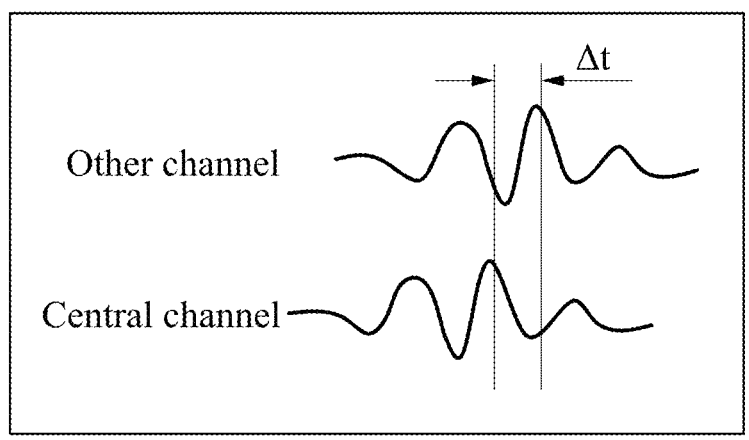

The aberration corrector 2004 may perform the aberration correction by cross-correlating a central channel signal to other channel signal to align the other channel signal with the central channel signal. For example, the aberration corrector 2004 may perform the cross correlation and adjust a delay ($\Delta t$) of the other channel signal as illustrated in FIG. 20C to align the other channel signal with the central channel signal.

Figure 20D:
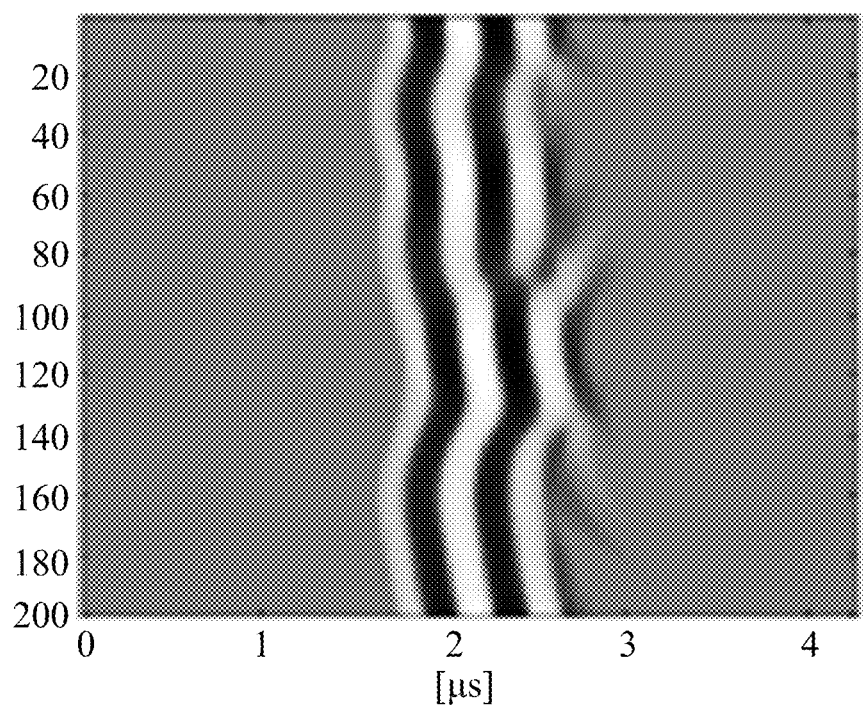
FIGS. 20D and 20E show images obtained prior to and subsequent to aberration correction based on cross correlation according to exemplary embodiments.
Figure 20E:
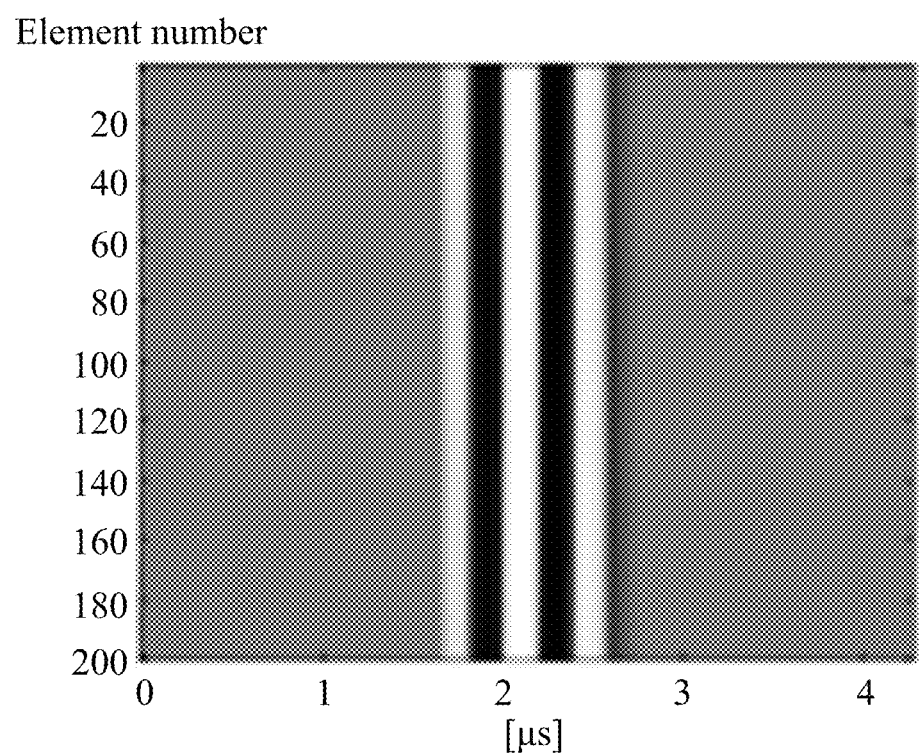

FIGS. 20D and 20E are images obtained prior to and subsequent to the aberration correction based on the cross correlation according to an exemplary embodiment.

Figure 21:
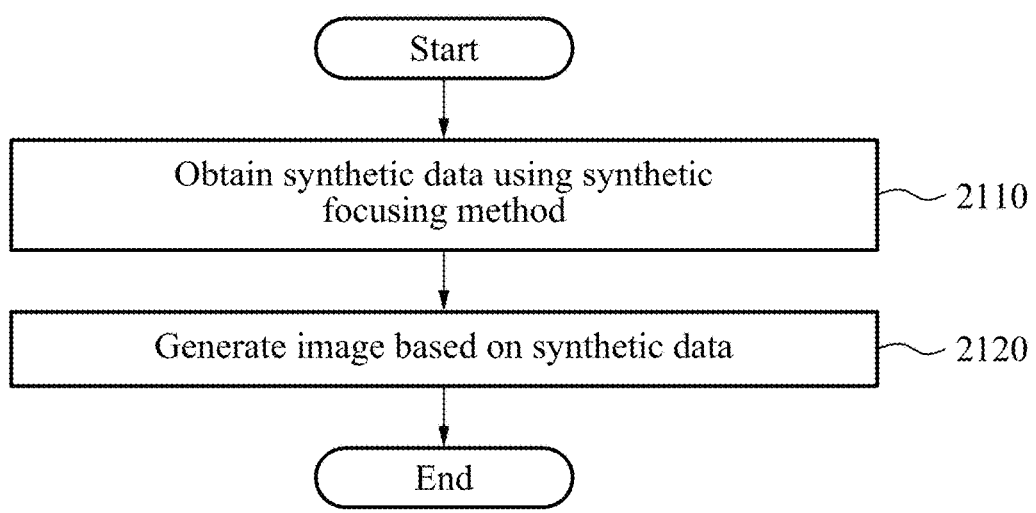
FIG. 21 is a flowchart which illustrates an ultrasound based measurement method according to an exemplary embodiment.

FIG. 21 is a flowchart which illustrates an ultrasound based measurement method according to an exemplary embodiment.

In operation 2110, the ultrasound based measurement method may obtain at least one set of synthetic data corresponding to at least one element of synthetic focusing point in a region adjacent to a reflector by applying a synthetic focusing method to received data corresponding to at least one actual focusing point.

In operation 2120, the ultrasound based measurement method may generate an image of the reflector based on the set of synthetic data.

The above-described exemplary embodiments may be recorded in non-transitory computer-readable media including program instructions to implement various operations which may be performed by a computer. The media may also include, alone or in combination with the program instructions, data files, data structures, and the like. The program instructions recorded on the media may be those specially designed and constructed for the purposes of the exemplary embodiments, or they may be known and available to those skilled in the computer and/or software art. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The media may be transfer media such as optical lines, metal lines, or waveguides including a carrier wave for transmitting a signal designating the program command and the data construction. Examples of program instructions include machine code, such as code produced by a compiler, and files containing higher level code that may be executed by the computer using an interpreter. The described hardware devices may be configured to act as one or more software modules in order to perform the operations of the above-described exemplary embodiments, or vice versa.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An ultrasound based measurement method comprising:
   performing ultrasonic beamfocusing on an actual focusing point;
   receiving data of an acoustic field reflected from a reflector in response to the ultrasonic beamfocusing on the actual focusing point;
   obtaining an element of synthetic data corresponding to a synthetic focusing point in a region adjacent to a reflector by applying a synthetic focusing method to the synthetic focusing point based on a first delay between the synthetic focusing point and the actual focusing point; and
   generating an image of the reflector based on the element of the synthetic data.

2. The method of claim 1, wherein the obtaining of the element of the synthetic data comprises generating a plurality of synthetic data sets using the synthetic focusing method, and
   the generating the image of the reflector comprises using the plurality of synthetic data sets.

3. The method of claim 1, wherein the obtaining the element of the synthetic data comprises:
   determining the synthetic focusing point in the region adjacent to the reflector; and
   estimating the first delay between the determined synthetic focusing point and the actual focusing point.

4. The method of claim 3, wherein the obtaining the element of the synthetic data further comprises:
   estimating a delay associated with respective transducers based on the first delay; and
   performing a delay correction on the received data based on the estimated delay, for the respective transducers.

5. The method of claim 4, wherein the obtaining the element of the synthetic data further comprises:
   determining a plurality of synthetic focusing points in the region adjacent to the reflector;
   performing the delay correction on each of the plurality of synthetic focusing points; and
   obtaining synthetic data sets corresponding to the plurality of synthetic focusing points, respectively.

6. The method of claim 1, wherein the generating the image of the reflector comprises:
   generating single channel data by calculating a sum of the synthetic data of each synthetic focusing point for each channel of a plurality of channels; and
   obtaining the image of the reflector based on the single channel data.

7. The method of claim 6, wherein the generating the image of the reflector further comprises:
performing aberration correction on the single channel data.

8. The method of claim 1, further comprising:
performing motion correction on the received data.

9. The method of claim 8, wherein the performing the motion correction comprises:
obtaining image frames of the reflector based on the received data; and
detecting a motion vector of the reflector by comparing the image frames.

10. The method of claim 8, further comprising:
calculating a delay error based on at least one of the synthetic focusing method and the motion correction; and
performing the synthetic focusing method repeatedly.

11. The method of claim 1, wherein the generating the image of the reflector is performed using the element of the synthetic data and the received data.

12. The method of claim 1, further comprising:
performing at least one of filtering and demodulating of the received data.

13. An ultrasound based measurement method comprising:
receiving data of an acoustic field reflected from a reflector;
performing motion correction on the received data by obtaining image frames of the reflector based on the received data, detecting a motion vector of the reflector by comparing the image frames, estimating a second delay between a location of the reflector prior to a motion and a location of the reflector subsequent to the motion estimating a delay associated with each transducer of a plurality of transducers based on the estimated second delay, and performing delay correction on the received data based on the estimated delay, for each transducer;
obtaining an element of synthetic data corresponding to a synthetic focusing point in a region adjacent to the reflector by applying a synthetic focusing method to the corrected data; and
generating an image of the reflector based on the element of the synthetic data.

14. The method of claim 13, wherein the performing the delay correction comprises:
performing the delay correction on the received data in a sampling section corresponding to an image frame at which the motion vector is detected, for each transducer, based on a location of the reflector in an initial image frame.

15. An ultrasound based measurement apparatus comprising:
a transducer configured to perform ultrasonic beamfocusing on an actual focusing point, and receive data of an acoustic field reflected from a reflector in response to the ultrasonic beamfocusing on the actual focusing point;
a processor configured to obtain synthetic data corresponding to synthetic focusing points in a region adjacent to the reflector by applying a synthetic focusing method to the synthetic focusing points based on a delay between respective synthetic focusing points and the actual focusing point, and
generate an image of the reflector using the synthetic data.

16. The apparatus of claim 15, wherein the processor is configured to generate single channel data by calculating a sum of synthetic data of each of the synthetic focusing points for each channel of a plurality of channels and perform aberration correction on the single channel data.

17. The apparatus of claim 15, wherein the processor is configured to generate image frames based on the received data prior to generation of the synthetic data, and
correct a motion of the reflector based on the image frames.

18. The apparatus of claim 17, wherein the processor is configured to compare the image frames and detect a motion vector of the reflector.

19. An ultrasound based measurement apparatus comprising:
an ultrasonic signal transceiver configured to transmit an ultrasonic signal to an actual focusing point and receive an acoustic field reflected from a reflector in response to beamfocusing;
a processor configured to generate image frames based on data received by the ultrasonic signal transceiver, estimate a motion of the reflector based on the generated image frames correct the motion of the received data based on the estimated motion, generate the synthetic data corresponding to multiple points in a region adjacent to the reflector by applying a synthetic focusing method to the data obtained subsequent to motion correction, generate single channel data by calculating a sum of the synthetic data for each channel and perform aberration correction, and generate an image of the reflector using the single channel data obtained subsequent to the aberration correction.

20. An ultrasound based measurement method comprising:
outputting a control signal which controls a transducer to perform ultrasonic beamfocusing on an actual focusing point;
receiving data based on an acoustic field reflected from a reflector in response to the ultrasonic beamfocusing;
obtaining synthetic data of synthetic focusing points in a region adjacent to the reflector by applying a synthetic focusing method to the synthetic focusing points based on a delay between corresponding synthetic focusing points and the actual focusing point; and
obtaining an image of the reflector based on the synthetic data.

21. An ultrasound based measurement method comprising:
outputting a transducer control signal which controls a transducer to perform ultrasonic beamfocusing on an actual focusing point;
receiving data with respect to an acoustic field generated by a reflector in response to the ultrasonic beamfocusing;
extracting a harmonic component from the received data;
obtaining synthetic data of synthetic focusing points in a region adjacent to the reflector by applying a synthetic focusing method to the synthetic focusing points based on a delay between corresponding synthetic focusing points and the actual focusing point; and
obtaining an image of the reflector based on the synthetic data.

22. An ultrasound method comprising:
determining an actual focusing point in a vicinity of a measurement point;
performing actual beamfocusing on the actual focusing point, by using ultrasonic transducers;
obtaining ultrasound data in response to the actual beamfocusing;

determining virtual focusing points in the vicinity of the measurement point, so that the measurement point is virtually surrounded by the virtual focusing points;

calculating synthetic data sets by adjusting delay of the obtained ultrasound data for respective ultrasonic transducers, in correspondence with the virtual focusing points;

adding the synthetic data sets for each of the ultrasonic transducers, to obtain single transducer data sets; and generating an image based on the single transducer data sets.

23. The ultrasound method of claim 22, wherein the calculating comprises:

estimating a first delay between corresponding virtual focusing points and the actual focusing point.

24. The ultrasound method of claim 23, wherein the calculating further comprises:

estimating a second delay associated with respective ultrasonic transducers based on the first delay; and performing a delay correction on the obtained ultrasound data based on the second delay, for the respective ultrasonic transducers.

* * * * *